(12) United States Patent  
Saavedra et al.

(10) Patent No.: US 12,374,207 B2  
(45) Date of Patent: Jul. 29, 2025

(54) ENVIRONMENT SENSING FOR CARE SYSTEMS

(71) Applicant: LogicMark, Inc., Louisville, KY (US)

(72) Inventors: Rafael Saavedra, Louisville, KY (US); Chia-Lin Simmons, Louisville, KY (US); Peter Williams, Louisville, KY (US)

(73) Assignee: LOGICMARK, INC., Louisville, KY (US)

( * ) Notice: Subject to any disclaimer, the term of this patent is extended or adjusted under 35 U.S.C. 154(b) by 0 days.

(21) Appl. No.: 18/757,139

(22) Filed: Jun. 27, 2024

(65) Prior Publication Data

US 2024/0346902 A1    Oct. 17, 2024

Related U.S. Application Data

(63) Continuation of application No. 18/104,117, filed on Jan. 31, 2023, now Pat. No. 12,094,313.

(60) Provisional application No. 63/328,101, filed on Apr. 6, 2022.

(51) Int. Cl.
```
G08B 21/02        (2006.01)
G16H 40/67        (2018.01)
```
(52) U.S. Cl.
CPC ............ *G08B 21/02* (2013.01); *G16H 40/67* (2018.01)

(58) Field of Classification Search
CPC ................................ G08B 21/02; G16H 40/67
See application file for complete search history.

(56) References Cited

U.S. PATENT DOCUMENTS

| | | | |
|---|---|---|---|
| 9,785,744 B2 | 10/2017 | Johnson et al. | |
| 11,172,854 B2* | 11/2021 | Tsuji | A61B 5/742 |
| 11,756,683 B2 | 9/2023 | Labarbera et al. | |
| 2002/0169583 A1* | 11/2002 | Gutta | G08B 21/0453 |
| | | | 702/188 |
| 2006/0033625 A1 | 2/2006 | Johnson et al. | |
| 2006/0252999 A1* | 11/2006 | Devaul | A61B 5/0024 |
| | | | 128/920 |

(Continued)

FOREIGN PATENT DOCUMENTS

EP    3838138 A2    6/2021

OTHER PUBLICATIONS

PCT/US2023/017558, "International Preliminary Report on Patentability", Oct. 17, 2024, 7 pages.

(Continued)

*Primary Examiner* — Mohamed Barakat
(74) *Attorney, Agent, or Firm* — K&L Gates LLP

(57) ABSTRACT

A system, apparatus, and method to monitor at least one person in at least one environment. The environment includes at least two sensors capable of detecting the presence of a person in that environment. The person under monitoring has a care condition to be monitored, where such monitoring involves the at least two sensors providing data sets to at least one signal monitoring system. Such data sets are communicated to at least one digital twin representing the person under monitoring and their environment, such that patterns of behavior may be determined for that person. Such patterns may be represented in the at least one digital twin, as to detect behavior that indicates a change in the care condition of that person under monitoring.

21 Claims, 10 Drawing Sheets

(56) References Cited

U.S. PATENT DOCUMENTS

| | | | |
|---|---|---|---|
| 2015/0350770 A1* | 12/2015 | Khenkin | H04R 19/005 |
| | | | 381/111 |
| 2016/0296160 A1 | 10/2016 | Larson et al. | |
| 2017/0319125 A1 | 11/2017 | Tsuji et al. | |
| 2018/0008169 A1* | 1/2018 | Chang | A61B 5/6801 |
| 2020/0289033 A1* | 9/2020 | Sivertsen | A61B 5/7275 |
| 2021/0327582 A1 | 10/2021 | Joshi | |
| 2022/0101710 A1* | 3/2022 | Tunnell | A61B 5/746 |
| 2022/0157143 A1* | 5/2022 | Panneer Selvam | G04G 9/007 |
| 2022/0280040 A1 | 9/2022 | Javed et al. | |

OTHER PUBLICATIONS

U.S. Appl. No. 18/104,117, "Non-Final Office Action", filed Apr. 19, 2024, 6 pages.
U.S. Appl. No. 18/104,117, "Notice of Allowance", filed May 31, 2024, 8 pages.
PCT/US2023/017558, "International Search Report and Written Opinion", Jul. 20, 2023, 8 pages.

* cited by examiner

Example wearable/carried devices and/or sensors worn or carried by Person Under Monitoring (PUM)

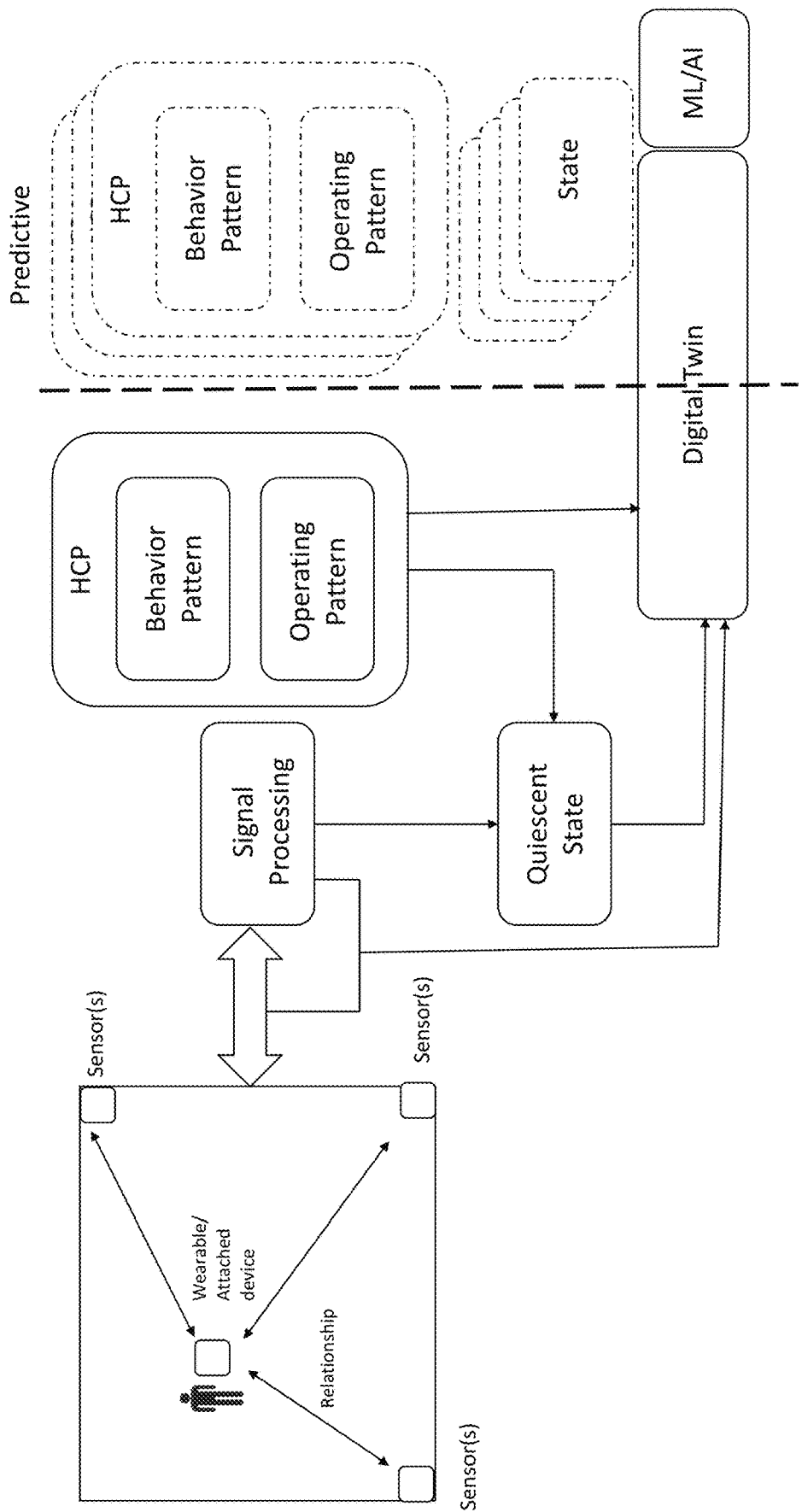

ENVIRONMENT SENSING FOR CARE SYSTEMS

CROSS-REFERENCES TO RELATED APPLICATIONS

This application is a continuation of U.S. application Ser. No. 18/104,117, filed Jan. 31, 2023, entitled "Environment Sensing For Care Systems," which claims the benefit to U.S. Provisional Application No. 63/328,101, filed Apr. 6, 2022, entitled "Environment Sensing For Care Systems," the disclosures of which are incorporated by reference in their entirety and for all purposes.

BACKGROUND

Field of the Disclosure

Aspects of the disclosure relate in general to a system to monitor a person under care.

Description of the Related Art

In traditional infrastructure technology environments, Personal Emergency Response Systems (PERS), also known as Medical Emergency Response Systems, allow persons to call for help in an emergency by pushing a button.

One example system is a two-way voice communication pendant that allows a person to call for assistance anywhere around their home. Personal emergency response devices make aging in place and independent living a possibility for persons under care. The personal emergency response device allows a person to remain connected with loved ones and emergency services through an existing landline telephone.

SUMMARY

Embodiments include a system and method to monitor a person under care.

A system monitors a person under care by at least one carer. The system comprises a care analytics management processors (CAMP), and a plurality of environmental sensors. Each of the environmental sensors including at least one elastic repository configured to store a dynamically configured predetermined amount of sensed data from an environment of the person under care. The environmental sensors are each connected to at least one computer-readable medium configured to store the sensed data generated by the environmental sensors. The environmental sensors are configured to sense the environment of the person under care, determine a quiescent state of the environment of the person under care, and detect an edge condition deviating from the quiescent state resulting in edge condition data. Upon detection of the edge condition, the environmental sensor is configured to evaluate the sensed data held in the at least one elastic repository and the edge condition to determine whether the environmental sensor changes an active state. Upon changing to an active state, the environmental sensor transmits a configuration specification to at least one other sensor in the plurality of environmental sensors in proximity to the environmental sensor. The environmental sensors in the active state transmit the sensed data and the edge condition data to the care analytics management processor. The care analytics management processor further comprises a transceiver and a microprocessor. The transceiver is configured to receive the sensed data and the edge condition data. The microprocessor is configured to determine whether a false positive situation has occurred. When the false positive situation has occurred, the transceiver is configured to transmit the configuration specification to reset the plurality of environmental sensors into the quiescent state. When a positive situation has occurred, the care analytics management processor is configured to transmit an alert to the carer.

In some embodiments, the transmitted configuration specification is based upon the edge condition detected by the environmental sensor.

In some embodiments, the transmitted configuration specification causes the at least one other sensor to dynamically invoke a threshold condition to detect the edge condition.

In some embodiments, the transmitted configuration specification causes the at least one other sensor to evaluate the elastic repository to determine whether the other sensor changes to the active state.

In some embodiments, the transmitted configuration specification causes the at least one other sensor to evaluate the elastic repository and the detected edge condition to determine whether the other sensor changes to the active state.

In some embodiments, the proximity to the environmental sensor is a physical distance.

In some embodiments, wherein the proximity to the environmental sensor is a logical distance.

In some embodiments, the proximity to the environmental sensor is based on line-of-sight.

In some embodiments, the quiescent state is based on the person's physical activity level.

In some embodiments, the alert is a telephone call, text message, or electronic message to the carer or emergency services.

In some embodiments, the elastic repository records at least 30 seconds of prior data. In some embodiments, the elastic repository records at least five minutes of prior data. In some embodiments, the elastic repository records at least one hour of prior data.

In some embodiments, the care analytics management processor is a wearable sensor configured to be worn by the person.

In some embodiments, the care analytics management processor determines that a false negative has occurred by analyzing the sensed data and the edge condition data from more than one of the environmental sensors.

In some embodiments, at least one of the plurality of environmental sensors is active emission sensor device configured to create a map of the environment. In some embodiments, the map of the environment is a 3-dimensional model. In some embodiments, the active emission sensor device is a radar device, Light Detection and Ranging (LIDAR) sensor, Radio-Frequency (RF) sensor, or Frequency-Modulated Continuous-Wave (FMCW) Radar sensor.

In some embodiments, the care analytics management processor is further configured to maintain an up to date and accurate positioning of objects designated by the person.

In some embodiments, at least one of the plurality of environmental sensors is a microphone, camera, strain gauge for impact detection, thermal sensor, motion detector, or haptic sensor.

BRIEF DESCRIPTION OF THE DRAWINGS

These and other aspects will now be described in detail with reference to the following drawings.

FIG. 10 illustrates the use of care village digital twins (701).

DETAILED DESCRIPTION

Aspects of the present disclosure include a system and method include an apparatus and method to monitor a person under care.

There are many sensors that may be applied to an environment to determine activities in that environment. These include sensors that actively transmit a signal into the environment, those that capture photons or other electromagnetic frequencies from the environment, those that capture acoustic and other air-pressure signals from the environment, those that capture motion in any direction, all of which can be portable and carried into the environment. There are devices that incorporate these sensors and others, such as accelerometers, gyroscopes, altimeters and the like in various combinations.

Figure 1:
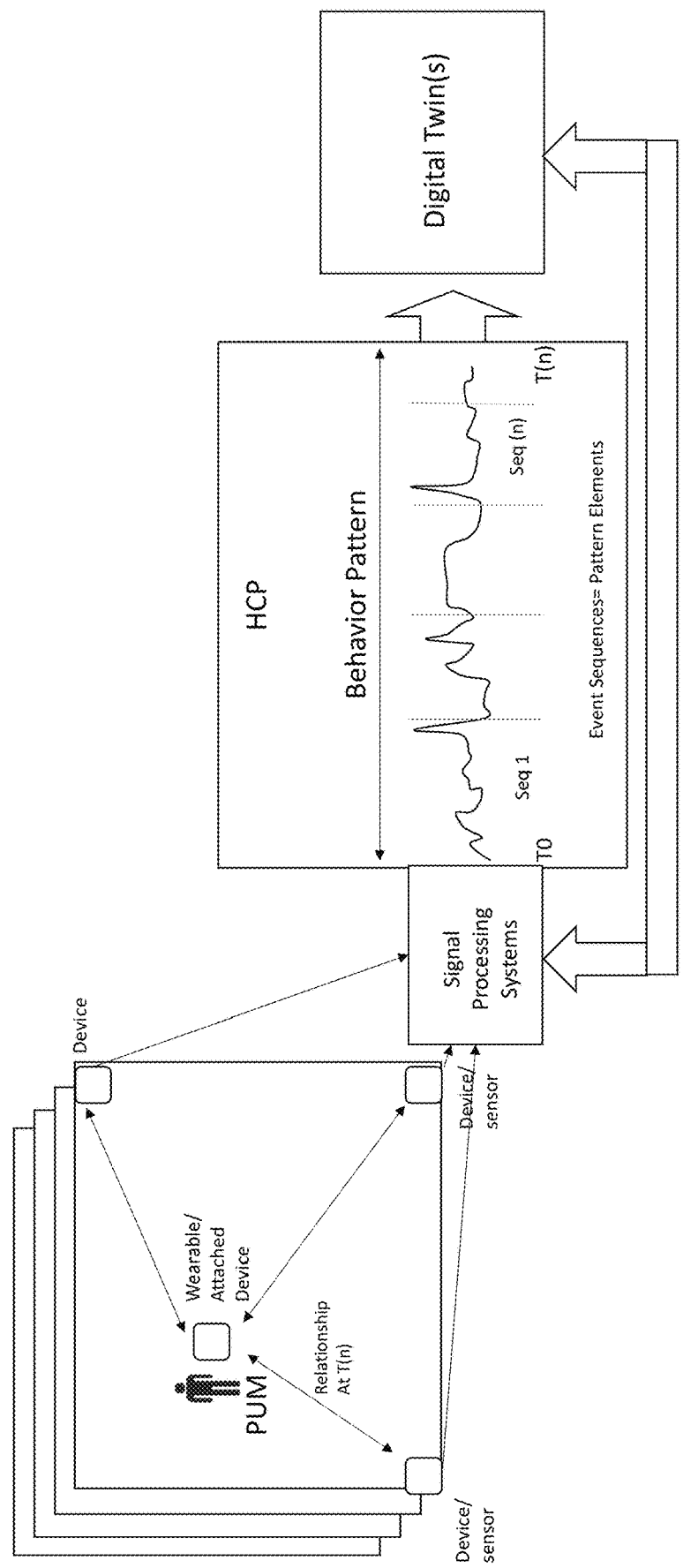
FIG. 1 illustrates a sensor enabled environment (102) in which a Person Under Monitoring (PUM-101) is domiciled

FIG. 1 illustrates a sensor enabled environment (102) in which a Person Under Monitoring (PUM-101) is domiciled. The data sets generated by such embedded (103) and/or carried or worn (104) sensors are communicated to one or more care analytics management processors (CAMP) (105) capable of determining behavior patterns (107) represented by that data. These patterns comprise, at least in part, representations of a PUM and their Health Care Profile (HCP-106) enabling the detection of their activities within the monitored environment in support of the detection and identification of one or more variations to those patterns that indicate a change in the care and/or wellness of a PUM. This data, patterns, configurations, specifications and any other management information can be stored and/or communicated to one or more care village digital twin (108).

In some embodiments the HCP comprises a framework that includes specifications for initial configuration of one or more sensors employed in monitoring a person specified in the HCP. This can include one or more care and/or wellness related specific behaviors, activities and/or events individually and/or in patterns. For example, a PUM with memory impairment may have certain sensors configured to identify repeated behaviors that indicate such impairment, including monitoring of any variance in the degree of such impairment. In another example, if a PUM, has a HCP that includes specifications as to the likelihood of a fall, then one or more sensors may be configured to identify behaviors that indicate an increase in the likelihood of that event occurring. An HCP can include patterns that represent the monitored behaviors of a PUM, such that variations from those behaviors may provide indications as to the likelihood or potential, (in some embodiments determined, at least in part, by one or more machine learning techniques) for a wellness or care event. In such circumstances the sensor configurations may be varied to configure the monitoring so as to accurately provide data to one or more response stakeholders and/or systems. This dynamic configuration of one or more sensors, devices and/or systems can provide further data that identifies a change in the behavior patterns for a PUM, which in turn may vary one or more configuration of a sensor, device and/or system, including for example providing such data to one or more stakeholders involved in provision of care and well-being for the PUM.

One aspect of data sets generated by the sensing devices can be classified as either constant or intermittent. Constant sensing, such as by a temperature gauge or barometer, simply captures the information created by the sensing capabilities and displays, stores and/or transmits this information. Intermittent sensing is undertaken on an activity, event, timer or other occurrence such as a request or interaction by a person, a trigger, periodic timer or other event activation, where the sensor data is directed to another device or system and/or the sensor itself is activated.

A further classification is of the sensors themselves, which may be either active or passive, in that the sensor generates or not one or more emissions A sensor can collect, measure, process, store and transmit data in any combination, depending on the capabilities of the sensor and the configuration employed. In some embodiments, a sensor can measure, store and/or transmit data based on the capabilities and configuration of the sensor. A sensor can be collecting and/or measuring or not, as determined by the state of the sensor, which in turn can be configured by the system. In some circumstances where a sensor is measuring, it may be configured to neither store or transmit any data unless or until a command, threshold or other trigger, action or event, including time, is received by the sensor and/or the systems controlling such a sensor. For example, a sensor may measure, store and not transmit any data or may be configured to transmit data on demand, such as when triggered either by specifications held by the device or on receiving a command from the system.

In some embodiments, sensors, devices and/or systems may employ one or more elastic repositories, where the storage available to that sensor, device and/or system may be dynamically adjusted from a minimum capacity to a capacity determined by one or more configurations deployed for those sensors, devices and/or systems. For example, a sensor is likely to have a fixed amount of storage incorporated into that sensor. This capacity may provide, for example, the capability to store up to an amount of data, which equates to a time period at a particular resolution on a continuous basis and/or the like.

The configuration of the sensor may include access to one or more further repositories that are connected to that sensor through one or more communications methods. For example, if a sensor is connected to a specialized hub, router or other device configured to accept such data from that sensor, the specialized device may provide an elastic repository that can dynamically provide additional storage capacity to that sensor. In some embodiments this specialized device is a care hub.

The determination of the available repository capacity can be expressed through one or more sets of configuration specifications, which may in whole or in part be determined by the operating pattern of the HCP. For example, if the state of the operating pattern is quiescent, then the storage capability provided may be configured to exceed that available on the sensor itself. This capability may be configured by the care hub, router or other specialized device to be a certain size of data and/or a length of time at a particular resolution. In this manner, the combination of sensors, devices and/or systems connected to one or more specialized devices, including care hubs, routers and the like, can provide data sets that inform as to the conditions prior to an event or alert being generated, by for example, an edge device, of a care or wellness event.

For example, if a PUM trips over a pet or furniture, certain sensors may detect a fall, whereas the situation was simply a minor trip, and as such the data prior to the event may confirm this is the situation, thus avoiding a false positive and potential unnecessary response.

For any one or more sensors, there is a quiescent state, from the perspective of the system monitoring the environment, where the sensor is either not providing any data to the system or the there is no change in that data. Sensors can have state, in that they are operating and at least one of collecting, measuring, processing, storing and/or transmitting data to the systems that have configured the sensor and established the command and control of the sensor operations.

Figure 3:
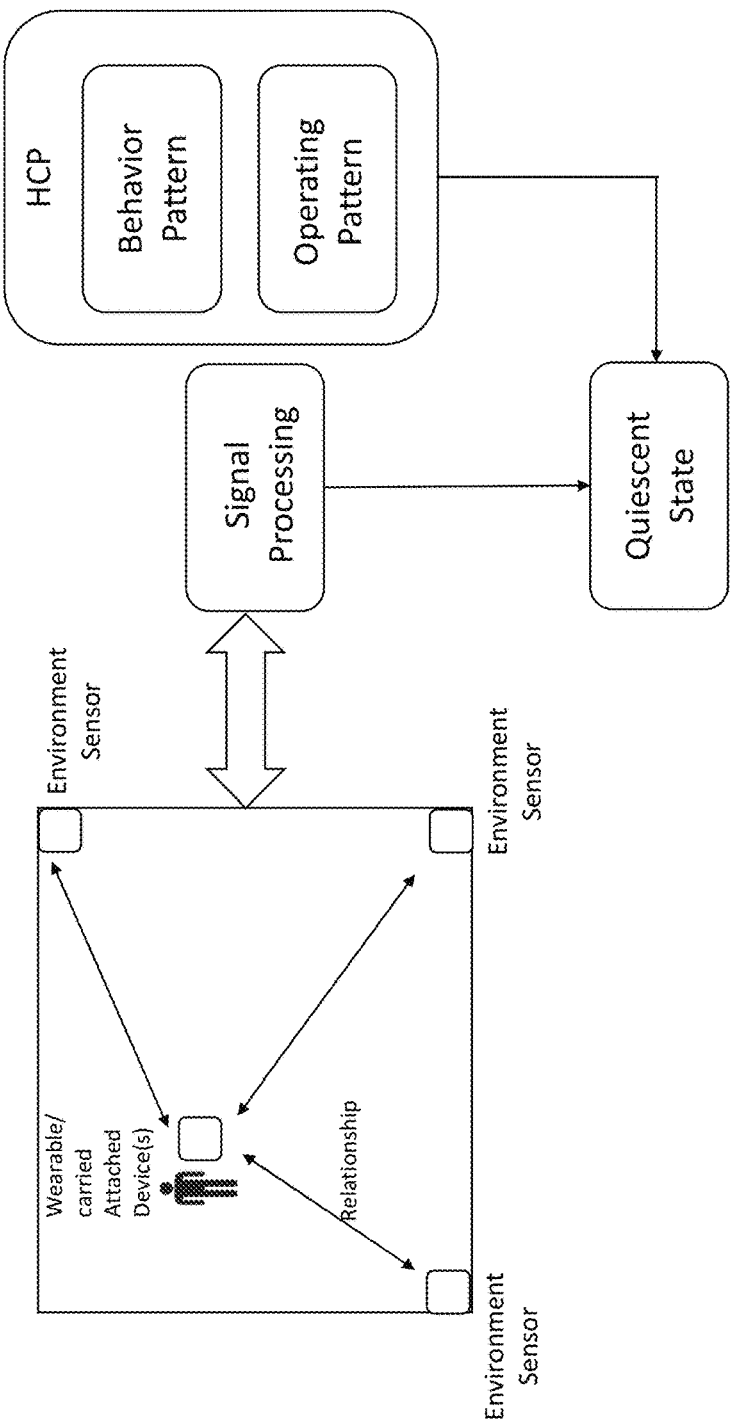
FIG. 3 illustrates an environment with a PUM (101), who has one or more attached and/or wearable device and/or sensor (104) in an environment (102) that includes one or more further sensors (103).

FIG. 3 illustrates an environment with a PUM (101), who has one or more attached and/or wearable device and/or sensor (104) in an environment (102) that includes one or more further sensors (103), all of which are configured by and managed, in part or in whole, by one or more care analytics management processors (105), whereby that system has established a quiescent state (109) for that PUM in that environment in the context of a HCP (106), that includes one or more behavior patterns (107), of which one or more is operating (108).

In an environment with one or more sensor, a quiescent state can be established by the system, using appropriate one or more care analytics management processors. This state may be determined from the data and/or may be established over a period where the data from the sensor is contiguously consistent with little or no variance.

In an environment with multiple sensors, each of these states of a sensor may in part be configured as part of a system to establish a quiescent state for a monitored environment comprising a number of sensors. This can include one or more sensors, measuring and sensing the environment. For example, there may be no transmission of data to other devices and/or systems from a sensor or set thereof, based on the state of the sensor and the environment, individually or collectively. This can include the sensor being inactive and operationally dormant or the sensors being configured to only transmit data on an event, trigger, threshold and/or action either generated externally, for example by the system, or derived from the sensor measuring and processing capabilities. The combination of states of individual sensors may be integrated such that a care analytics management processor, which can incorporate one or more command and control function set, can configure their operational state and/or manage which sensors may communicate with other sensors to vary operating states.

Sensors may be integrated into devices. For example, a typical smartphone can have multiple sensors embedded within it. In other examples a sensor may be stand-alone device with a single function, such as a Micro-electromechanical systems (MEMS) microphone intended to capture acoustic signals. Such stand alone and/or single function sensors may be aggregated to form sensor sets that have greater capabilities than a single sensor.

In some embodiments, a sensor may be capturing data from an environment and such data may be stored by the sensor. This can include the sensor having sufficient onboard storage capability and/or access to a repository suitable for such data storage. This data may be stored on any type of basis, such as FIFO, where the data representing a particular length of time, period of a day, quantity of data or other metrics, is be stored in the repository. The data set from any sensor may be configured to be stored for a period of time, up to a quantity of data, until an event or message is received, until further configuration specifications are deployed and/or other conditions and/or specifications are invoked.

In this manner a sensor may retain a set of data, that when an event occurs, can be accessed to ascertain the conditions represented by that data prior to such event. As there can be multiple sensors deployed in an environment, the data from such sensors when combined can provide a valuable insight and context to the event. For example, this can be particularly useful in detection of false positives or provision of data that can assist an emergency or other responses. For example, breathing difficulties may be detected through the combination of sensors prior to a fall potentially indicating the cause of the fall.

In the case of passive sensors, they may be collecting data on a continuous basis and storing that data, for example for a configured predetermined time, e.g. 15 minutes, after which the data is deleted from the sensor repository. If the sensors are active, that is they use emissions to create data sets, such as FMCW RADAR and the like, these sensors may be configured to undertake periodic emissions as part of the monitoring pattern that is operating. The data so generated may be stored in a repository in a manner similar to the passive sensors.

In some embodiments there may be one or more device, described here as the edge device which can initiate the change of state of at least one other device from a state, for example, from quiescent state to an active state, to another state. Such an activation may be initiated through a sensed event, a timed and/or configured arrangement and/or through a pattern specification that includes such one or more event. These activations may involve a common system integrating the sensors, such as a command and control system and/or may use direct communications between the sensors based on, for example an appropriate protocol and security schema.

In some embodiments, an edge device may be a device set comprising at least two devices produce an event signal that activates a processing step that changes the state of at least one other device. This processing may be undertaken on the device and/or may be undertaken on one or more server in any arrangement.

In this manner a combination of a specifications of a pattern and one or more environment sensing device may be combined to change the state of one or more other sensing device. This state change may include varying the configuration of the sensing device, such that the capabilities of the device are focused on a specific event type, behavior pattern and/or other focal point.

In some embodiments, a combinations of sensor data may be created through augmentation of a single sensor with capabilities of another sensor. For example, an acoustic sensor, such as a MEMS microphone attached to a hard surface, for example a window, can have a frequency response configured for detection of low frequencies, for example such as footfall of a person under monitoring (PUM) and as such may collect, measure and process a detection, and create an event. For example, the initial sensors may detect an acoustic signal which is matched to a pattern that is specified as a "trip," where for example, a PUM misses a step, which could indicate the PUM is unstable and is about to, or is in the process of having a fall. Such an event can then trigger other devices, such as smart speakers, smart phones, smart TVs and the like to turn on their microphones, screens, speakers or other capabilities and in those cases where the capability exists provide stored information, such as that which is buffered or cached, that is prior to the event captured by the first sensor that created the event, which may then be combined by the system to create a richer data set for analysis by care analytics management processors.

Additionally, some sensors may have relationships with other sensors, such that the relationships are preconfigured in an arrangement such that on an event being detected or triggered directly or through a communication method, the sensors provide data sets to each other and/or to a monitoring system. For example, if a sensor is triggered or detects an event, other sensors may provide data sets that enable the initial sensor or any sensor in such an arrangement to undertake and/or provide additional capabilities suitable for enhancing, expanding and/or extending the data set that can then be provided to one or more care analytics management processors In the example where one of the sensors in this arrangement is configured as an edge device, this may cause the other devices in that arrangement to vary their configuration in response to the edge device communications. Such communications may vary in-line with the edge device sensing capabilities, such that on detection of certain types of events, which may be specified as patterns, stored locally on the sensor or host device or in a repository that is available to that sensor or host device, the edge sensor may send differing communications sets that include instructions for configuration of the other sensors. In some embodiments such communications may be in the form of tokens. The capability for a sensor and/or device hosting or connected to that sensor to send configuration data to another sensor, with which the first sensor is in proximity, enables a set of sensors to adaptively respond to a change in state of a PUM and/or the environment in which they currently occupy.

In some environments there can be a sensor designated as a dedicated edge sensor that is configured to capture an event that indicates a change in the state of that environment from quiescent to an active monitoring state. For example, this can be a motion detector, acoustic detector, camera and/or the like. Such configured edge detectors may have configurations that are respectful of the privacy of a PUM. For example, if a PUM uses a bathroom, a camera is an inappropriate sensor, where as a motion detector or MEMS microphone configured to detect footfall, or a strain gauge configured to detect pressure on the floor can be more appropriate and can provide the initial signal for that change of state. In some embodiments the sensor can incorporate one or more event data sets which represent such events and/or may be configured to be triggered by one or more events that exceed one or more thresholds or other configuration specifications.

Figure 6:
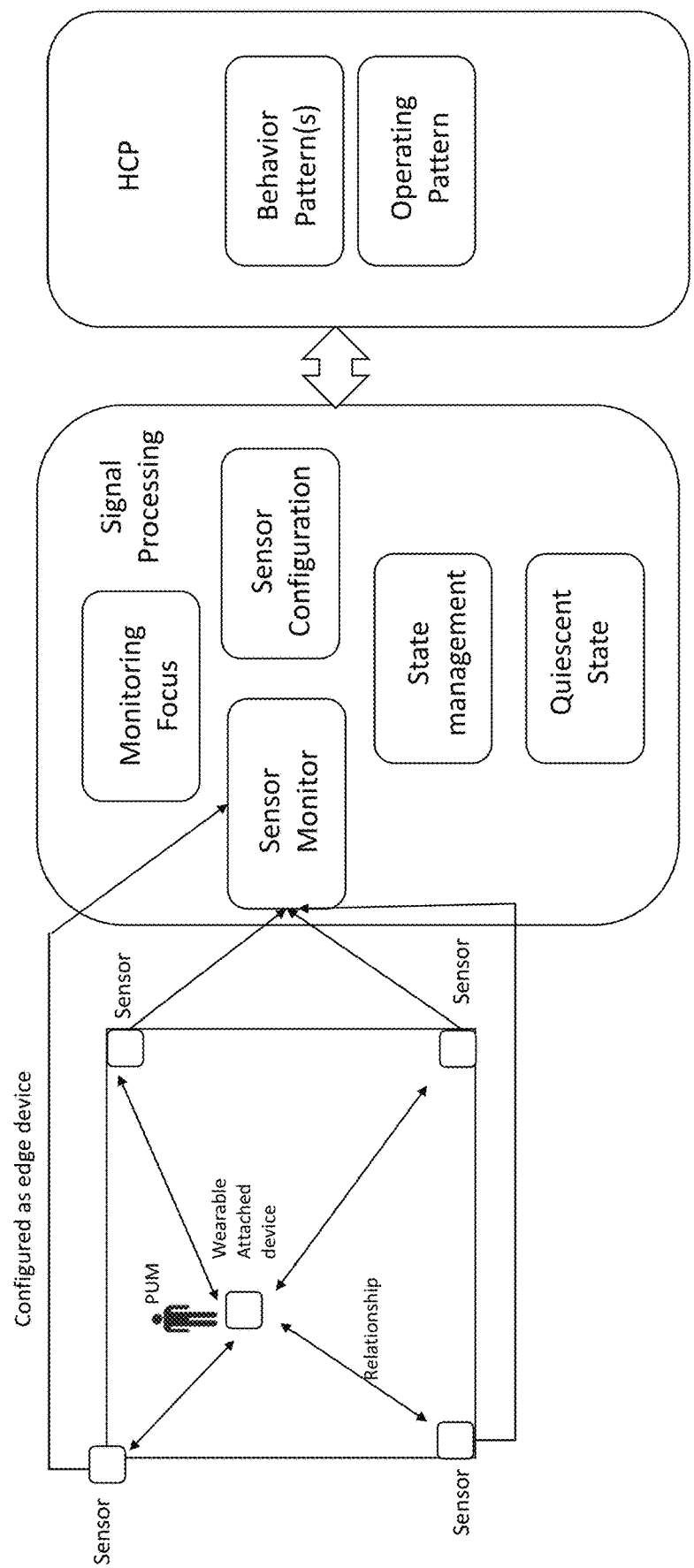
FIG. 6 illustrates one or more sensors configured as an edge device for monitoring a PUM in an environment.

FIG. 6 illustrates one or more sensors configured as an edge device for monitoring a PUM in an environment. A PUM (101) in an environment (102), which includes one or more sensors (103/104), one of which is designated as edge sensor (110), such sensors providing data to one or more care analytics management processors (CAMP) (105). In this illustrative example, care analytics management processor (105) includes sensor monitoring (112), sensor configuration (113), monitoring focus (111) and state management (114), all of which can be embodied as modules of one or more care analytics management processor. The state management module may instantiate and/or store and/or retrieve a representation of a quiescent state (109) of the monitored environment. The care analytics management processor can communicate with the HCP (106), which includes behavior patterns (107) and operating patterns (108) in any arrangement.

This can lead to arrangements of edge devices that support the monitoring of the PUM to instantiate behavioral patterns (108) for a PUM, whilst not being invasive of the PUM's privacy.

In many circumstances it is possible to create false positives, where a single device detects an event, for example the sound of something falling, which then can trigger a response. The use of edge sensors to interact with other sensors, devices and/or systems to ascertain the accuracy of a situation is highly beneficial. This may occur through activation of differing sensors, for example a camera, microphone and/or other device. The data generated can then be combined with the initial edge response and evaluated by a monitoring system and/or by a human operative. In some embodiments the initial evaluation may be undertaken by comparing the individual and combined responses of the sensors with a pattern that is indicative of the type of situation, for example stored as a pattern or anticipated occurrence for that person in that environment. This can include, for example patterns that are indicative of a fall of a person, misstep, breathing anomalies, breakages or other occurrences that collectively and individually indicate that a PUM is having, or is likely to have an incident that impacts their care and/or wellness.

In some embodiments, those devices capable of two-way communication, such as a cell phone, smart speaker, smart TV and the like may be configured to initiate an interaction with the person occupying that environment. In this manner the person may communicate with the system monitoring the environment, where that system may include an ML function to evaluate the communication and/or include one or more human monitoring of the environment. For example, a device capable of producing an audio signal, may ask the PUM a question, such as "are you alright" or similar, and then using either that device or other sensors or devices in the environment, listen for a response for the PUM. This response may be evaluated by voice pattern recognition systems to ascertain the degree of stress in the PUM's response, which may then cause further system responses, for example, a carer may call, message and/or visit the PUM and the like.

Creation of patterns from sensors that are integrated into an environment, which can include feature extraction as a sub set thereof, can enable the extension of the features of a sensor, where the capabilities of the sensor may be expanded and/or extended through integration with other sensors in proximity and/or through deployment of configuration specifications for that sensor as specified by one or more pattern. This can include the use of ascribed value and weighting of a particular feature that is being evaluated by the combined context rather than by the sensor itself. This extended and/or expanded data set can be integrated into a pattern and/or context. There may be one or more thresholds, managed by the sensor directly and/or in combination with other systems, that can be dynamically invoked. These thresholds may then trigger the expansion and/or extension of the sensor, including combinations of other sensors in proximity. This enables the evaluation of a single data set, for example a feature extracted from an image recognition system to be incorporated into a pattern that more accurately represents the situation occurring in a monitored environment. This can reduce the occurrence of false positives or negatives that often are caused through the evaluation of a single data set in isolation from the context in which it occurs.

Although there has been significant development in the field of autonomy, especially in mobility, the care village environment sensing systems, which are predominately self-adaptative, dynamic and responsive, are not initially intended to be fully autonomous. The care village systems are intended to incorporate one or more autonomous sub systems, as for example a robotic medicine dispenser, where these specialized function systems become part of the monitored environment. As autonomy becomes more prevalent and reliable, the integration of autonomous sub systems will likely increase without a detrimental effect on the wellness of the PUM.

Figure 2:
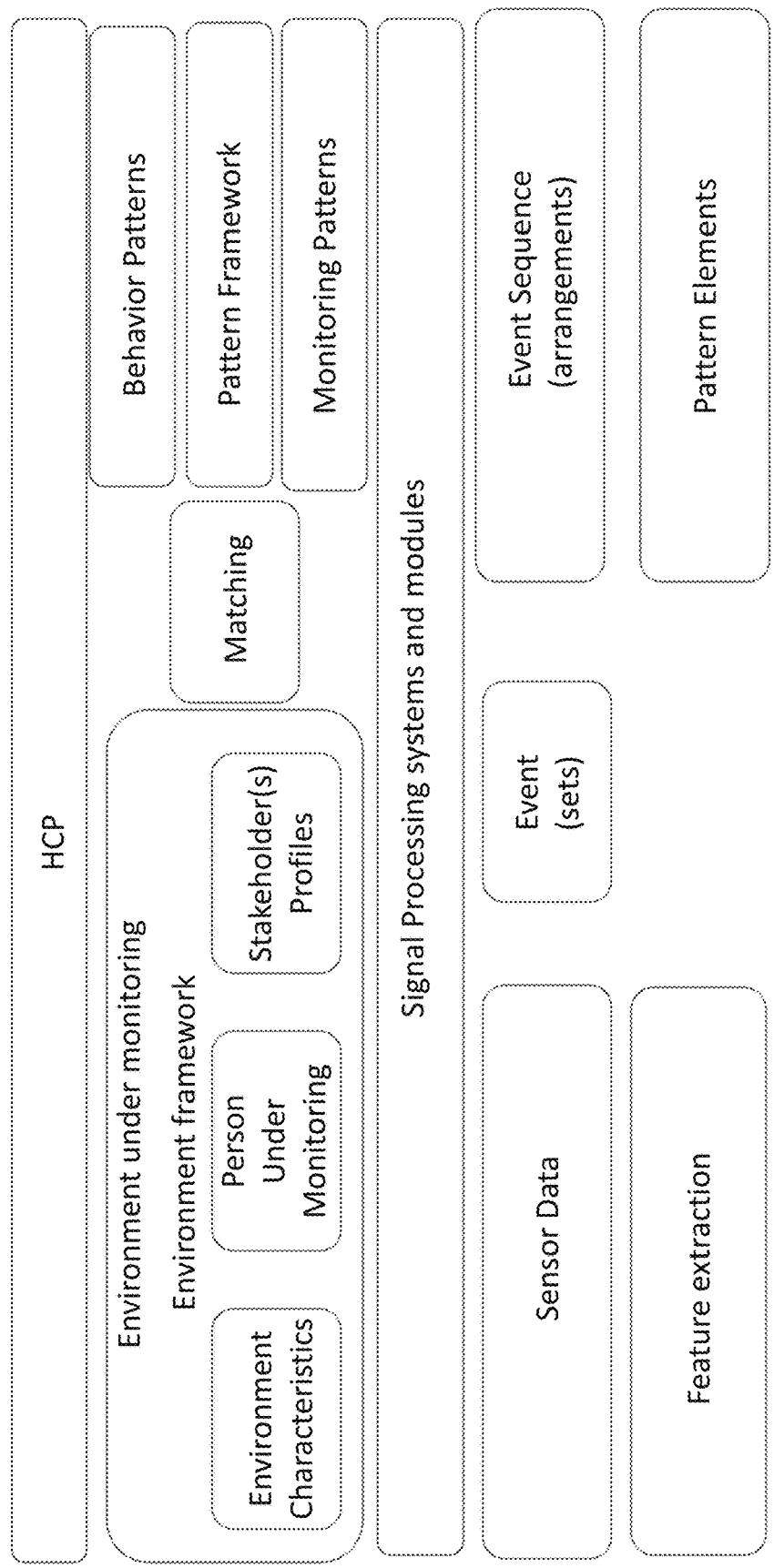
FIG. 2 illustrates an example set of modules that in combination provide a system for the monitoring of a person under care.

FIG. 2 illustrates an example set of modules that in combination provide, at least in part, a system for the monitoring of a person under care described herein. An HCP (106) communicates with the environment (102), which includes environment characteristics (201), the profile of a PUM (211) and other stakeholder profiles (202). This can include an environment framework (212). The system can include one or more sets of patterns, which includes one or more pattern framework (204), behavior patterns (107) and operating patterns (108), which can be matched, using a matching system (203) to an environment (102) and the elements thereof. A care analytics management processor (105) can be in communication with all these system elements and may include one or more sensor data repository (206), feature extraction systems (207), event sets (208), event sequences (209) and pattern elements (210) in any arrangement.

Environment Specifications

In some embodiments, an initial survey of an environment is undertaken to ascertain the characteristics of that environment, including the physical attributes, such as dimensions, entrances, windows, floor coverings, furniture (fixed and movable), and the like including the facilities of that environment, for example, electrical outlets, plumbing, climate control and the like. The survey can also include an inventory of the furnishings of the environment and their locations within that environment, including those areas of the environment with specific purpose, such as bathrooms, kitchens, bedrooms and the like. This survey may be undertaken directly and/or may be based on architectural or other existing plans. This survey can also include devices capable of sensing that environment.

In some embodiments a set of sensors, including those within the environment, can be used as part of the survey, to create an environment data set incorporating multiple perspectives from a range of sensors with differing capabilities. For example, cameras or other photon capture devices provide one perspective at visible light wavelengths, audio transmissions and receiving sensors and devices can provide a further perspective data set and FMCW or other RADAR or LIDAR sensors and devices can provide further data sets.

These data sets are then integrated to form a comprehensive survey and/or mapping of the environment establish the boundaries and contents in a manner that can be used by the care village systems. This can include multiple passes by differing sensor sets to establish with a high degree of accuracy the location, physical characteristics and other aspects of the environment and the contents thereof.

The sensors may be invoked in real time for additional verification and accuracy or may be used to update the survey if a change in the environment is detected.

These environment survey characteristics are then stored by the system in one or more repositories as the specifications of the characteristics of that environment. Initially this information is stored as an Environment Framework. Such specifications may be used by the system to calculate various attributes of the environment, such as the potential acoustic fingerprint of the environment, the temperature of the environment at differing times and seasons, the humidity or other aspects, and the like. This can include, for example, the type of floor covering, amount and location of soft furnishing and the ratio of hard to soft surfaces. The physical characteristics of the person or persons occupying the environment will also be a factor in establishing these characteristics.

The framework provides an initial representation of the environment, and in multi room and/or environments with a bounded outdoor space may incorporate those as part of the Environment Framework (ENFW). This initial ENFW can then be populated over time with the data sets from the sensors embedded in and/or traversing that environment. One aspect of this is establishing the at rest state of the environment, which can inform further evaluation of occurrences within the environment, and can, in some embodiments be considered as the "noise floor" against which any occurrence detected by a sensor can be evaluated.

In some embodiments an active device that can include one or more sensors may be used in that environment to ascertain specific properties of that environment, for example a wide band acoustic transmitter may be used to determine the acoustic properties of that environment. Such devices may also be used to determine common acoustic signals for that environment, such as door or window opening or closing, chairs being moved and the like. These factors may also be calculated using Machine Learning techniques and may form a signature that is used in the appropriate signal processing to enhance the efficiency of that processing. For example, removal of potential false positives through activation of additional sensors, and/or through variation of the acoustic properties of the environment so as to enhance detection of any signal commensurate with a change of state in that environment.

Similar techniques may be employed for other frequency and time domain characteristics, for example at the visual, infrared and ultraviolet wavelengths, RF wavelengths, RADAR, LIDAR and the like. This may include using laser or other forms of coherent wave front technology to establish the baseline characteristics of the environment, for example walls or other boundaries to measure distances and the like. This can include identifying differences in height of surfaces, such as stairs or floor height differences. Such characteristics may then be classified as trip hazards or other potential aspects that may impact the well-being of a PUM.

An inventory of devices, such as electrical devices, fridge, room cleaning or other autonomous, semi-autonomous and manually operated devices can also be stored as part of the environment specifications. In some embodiments, the system may use generic characteristics of such devices as placeholders within the specifications and then test these as hypothesis against the actual sensed information that is monitored to form a more accurate representation of the environment. Where available the specifications of an actual device may be incorporated into the ENFW, for example the power or water consumption, time of operation and/or other directly or indirectly observable characteristics of the devices may be included.

Identity

There are a set of identities that are instantiated and deployed by the system for the provision and management of care to one or more persons. The identities are unique to the system and in some embodiments may employ distributed ledgers and/or other immutable record systems. The system may assign identities to each sensor, device, environment, stakeholder or other care village entity in any arrangement. These identities may be instantiated as immutable identifiers, that is the representation of an identity by an identifier. In the case of humans, this may incorporate biometric and other person specific identifying characteristics, such that the identity of, for example a PUM, as represented by their identifier, can only, when evaluated by one or more systems, be satisfied by that specific PUM. Specific characteristics and/or other meta data, including contextual, location specific, temporal and the like, can be used in conjunction the identifier of the care village entities, such as sensors, devices, environments and the like.

In some embodiments a PUM who has a system issued identity can have relationships with one or more other system elements, such as environments, stakeholders, devices, tokens and other system entities and/or their respective digital twins. This relationship can be implicit or explicit, and as such can form an identity context for that PUM. Such an approach may be used by the care village systems to establish further identity characteristics, including those of a dynamic nature, for example when a role, for example a carer, is being fulfilled or when the interaction, invocation and/or involvement is on a temporary basis by another stakeholder.

Such a context may be embodied, for example, as a matrix or other formalism, including graph, vector or other spatial and/or temporal representations, where each of the identities has at least one relationship with another identity. For example, this can include a PUM and their respective environment and the sensors and devices embedded with that environment and/or those devices a PUM may carry with them. This can also include the relationships with other persons, such as family, friends and/or care providers or enablers.

In some embodiments, these relationships may include specifications that, at least in part, determine the use, distribution, privacy, processing and/or other system capabilities and functions, including capabilities and/or configurations, that may be applied to these relationships, by the care village systems and/or the identities therein. Such configurations may be applied dynamically in anticipation of and/or in response to one or more data sets provide by one or more sensors, devices and/or systems.

The system creates and deploys one or more identity, which may be immutable, for an environment. This identity can be in the form of a token, which can include a cryptographic representation and can be stored in at least one distributed ledger and/or other storage system. Such an identity may include an organization of the elements comprising that identity, expressed as an identifier, such as a hierarchical or other arrangements, which can include differing regions or elements. For example, this may include separate identifiers for differing rooms in a multi room environment and the like. In some embodiments, the devices and physical artifacts of that environment may also be given identities, which may be arranged in a hierarchical or other organizations.

The structure of these identity arrangements may form a schema which is used by one or more services and/or systems when interacting with these identities. In some embodiments, such schema may be dynamically created and deployed on a set of identities in response and/or in anticipation of one or more state changes involving at least one of those identities.

Stakeholder Specifications.

There can be any number of stakeholders that can participate in a care village. This includes one or more stakeholders that include the Person Under Monitoring (PUM). Stakeholders can include individuals, organizations, groups of individuals and/or organizations, roles, classes and/or types of roles, such as functions and the like. There may be multiple organizations of Stakeholders where each of the stakeholders has a relationship with other stakeholders, for example as an ontology or taxonomy. For example, each of these PUM will likely have a set of other stakeholders with whom they have relationships, that can include for example, professional relationships, such as doctor, dentist, physical therapist, care giver and the like, and other relationships, such as family, friends, neighbors and the like.

Each environment has at least one or more person, a stakeholder, who is predominately present in that environment, in that they are domiciled in that environment on a permanent or temporary basis. This stakeholder is the person under monitoring, PUM. There can be multiple PUM domiciled in a single environment, for example a couple. Each of these stakeholders has a set of characteristics, including their physical attributes, such as height, weight, gait and other characteristics that form the basis of the system stored biometric specifications for that person. This may include other biometric and/or care related characteristics, including health conditions, which have been previously recorded, such as blood type, eye color, hair color and the like.

For example, where a PUM is to be or is under care of the care village systems for health and/or wellness monitoring, their confidential health records may also be made available, in whole or in part, to the system. Such availability may be subject to one or more mandated privacy or security regimes. In some embodiments this may include the use of secure tokens. In many circumstances a specific health or wellness condition is the initial reason why the PUM is being monitored by the system. This condition, described as the primary condition, can determine, at least in part, the configuration of the monitoring arrangements for a PUM. However, as is often the case, the primary condition may have other health and care related aspects that can have consequences for the PUM, and as such the systems can be configured to monitor for any behaviors and patterns that have a care or wellness impact.

There is a system initialization set of processes where the identification of the environment, stakeholders, including PUM and their primary condition and/or other health or care related conditions, are created as system elements. This forms part of a PUM's Health Care Profile (HCP).

Each of these stakeholders may have a relationship with the person and/or the environment which has certain characteristics, some of which form patterns of behavior and interaction that may be used by the systems for the provision of care monitoring.

These relationships may be represented in the form of bilateral or multilateral specifications, where the exchange of information between the parties is governed by these specifications. In many embodiments, this will involve device to device, sensor to device, sensor to sensor data exchange, where the is a mutual agreement, which may be binding and includes, for example, smart contracts and the like, between the devices. In some circumstances these may operate as representatives of the stakeholders, with one or more sets of specifications governing to what extent and/or the content of the data that is or is anticipated to be exchanged. The exchange can be specification and/or context dependent and/or impacted by the current state of the environment and the one or more persons therein.

As the PUM is effectively a focal point for the care system, the degree of data about their current condition, is likely to be more detailed, especially in terms of their health and wellness condition(s). This health and wellness data is likely to initially be the reason that they are placed under monitoring.

Stakeholder Profiles

Each stakeholder in the system is issued with a system unique identity. This identity can provide for multiple relationships with other stakeholders, sensors, devices, environments, care systems and the like, in any arrangement. Common approaches such as the use of NFT or other cryptographic tokens may be employed for both security, reliability and integrity of the identities and the privacy of the individuals represented by such identities. These identities may include multi factor authentication, such as typical two factor, biometric multifactor, location and other contextual data, so as to ensure that each stakeholder is accurately and reliably identified in manner that protects both the stakeholder and the care village from false or inaccurate representation of identities, such as typical phishing or other false identity representations. This includes ensuring the minimal burden on a PUM or other stakeholder to establish, validate, and authenticate that identity.

Such identity systems may use one or more biometric features as part of the identity representation, which can include fingerprint, retina scan, face recognition, gait analysis, palm recognition and/or other biometric data in any combination. This can include one or more sensors and/or devices that are similarly identified through specific features and identifiers of those sensors and/or devices, including confirmation of the relationship of a PUM to those sensors and/or devices, which in turn may include biometric data, as a proxy for that person for interactions with the one or more care village systems. This can include multiple devices, each of which is authenticated to one or more care village systems and/or to other devices, forming a set of data, expressed as a profile, that has co-location, proximity (physical or logical) and/or other characteristics that can be validated by one or more other sensors, devices, stakeholders and/or care village systems. For example, a PUM may have a PERS which is worn, and the state of being worn can be confirmed by the PERS, and/or through other sensors and/or devices. The PERS may be an independent device and/or can be a smart phone, that is configured to act as a PERS, through the onboard sensors of the smartphone. These devices, PERS and/or smartphone, separately or together can communicate, for example using Bluetooth, to provide a set of data, for example in the form of one or more tokens, to a third device, for example a router capable of receiving Bluetooth communications, which then communicates with one or more care village systems.

Such identities may be represented in one or more Care Village Digital Twins (CVDT's), and may be used by the care village systems as part of the evaluation and analytics for a PUM and their environment. In this manner the CVDT evaluations, modelling and/or predictions may include, for example, changes in the cadence of patterns of behavior of a stakeholder to more accurately represent those behaviors of a PUM.

Stakeholders may have active or passive participation in patterns and/or response arrangements that are or can be deployed in an environment. This can include the multiple and sometimes complex relationships between the individual stakeholders and their impact on the PUM.

An aspect of the system is ability to undertake verification that certain care and wellness related activities have been undertaken, for example scheduled or prescribed visitations by care and health stakeholders, as well as systems acting as proxies for those stakeholders. This can include devices that dispense prescription medicines and the like. For example, this can include regular PUM self-care, such as showering, regular sleeping, exercise and the like, as well as the taking of prescribed or other medicines in the manner that is specified. Many of these actions can be identified by at least one sensor, either directly and/or through inference, so as to verify or not that the action occurred, the timing, context and other data as appropriate. One of the verification techniques is the use of proximity, that is a care provider and PUM are collocated in an environment. This can include device to device communications, using for example, Bluetooth, where the distance is calculated through monitoring of signal strength. The use of near field technologies, such as NFC and/or RFID may also be deployed, as can line of sight and/or other directed proximity techniques. The near field techniques may include the use of smart cards or other near field enabled devices, where the device and/or card needs to touch a reader for confirmation. For example, an environment may have a fixed terminal for such transactions and/or a PERS may be configured as a mobile terminal for this purpose. In some embodiments it may be sufficient to detect and/or confirm the presence of one or more stakeholder, whereas in some circumstances more stringent confirmation of the colocation of the one or more stakeholders may be required. For example, the use of camera's, radar, heat or thermal detection and the like may be used to confirm, verify or ascertain the proximity of one or more stakeholders to another stakeholder, for example the PUM. In some embodiments one or more devices may use dynamic QR codes or similar barcode and/or other visual indicia to ensure the proximity of one or more devices. These devices may be coupled to their respective owners such that there is a confirmation of the owner's presence, through for example, fingerprint, camera or other biometrics and the generation and reading of such indicia within a certain timeframe.

Included in this approach is the use of one or more biometric techniques that can verify the presence of one or more stakeholders. This can include the use of short range communications, such as Bluetooth, near field and/or high frequency RF communications, such as 60 Ghz, for example using a smart device and/or a PERS configured for such short-range communications.

Such verification can include one or more sensors providing data sets that indicate such an event is being undertaken, such as a shower being run, a toilet being flushed and the like. Such indications may be detected by audio sensors for the initial indication, and then confirmed by, for example an increase in water flow being measured. Each of these activities has a different profile both in terms of audio and water usage, which enables the detection of such an event with high confidence. This data may be used, in whole or in part, as part of one or more patterns indicating behaviors of one or more stakeholders in one or more environments. The monitoring of services, such as water, gas, electricity, internet and the like may be integrated into a behavior pattern for a stakeholder.

In some circumstances, specialized devices and/or applications may be used for the dispensing of prescribed or other medicines. These devices and or applications may be integrated into the environment and the data sets generated by such devices can be complimented by further data sets from other embedded sensors. For example, the detection of water flow or a fridge door opening, for example using MEMS microphones or other acoustic and/or other sensors, can add veracity and confidence to a data set indicating that a PUM took their medications at a specific time.

The use of multiple sensors for detection of events and actions that are then confirmed by one or more other sensors enables the generation of data sets that can be relied upon due to the increased accuracy of the one or more confidence and/or probability metrics for that data.

Environment Sensing

The relationship of a PUM to their predominant domicile environment can form the basis for a comprehensive set of reliable behavior patterns for that PUM and the environment. A key aspect of the system is establishing the states of the PUM in that environment so as to be able to determine with a high degree of accuracy the behaviors of that person within at least one specific pattern of that behavior. To achieve this degree of accuracy the environment is sensor enabled so as to generate data sets that establish the context for these behavior patterns.

Using one or more classes of sensors capable of active emission technologies, such as RADAR, Light Detection and Ranging (LIDAR), Radio-Frequency (RF) and/or audio and/or other emission-based sensing technologies may be used to create a representation of the environment under monitoring. These emissions may be combined to create a 3D map of the environment including any fixed features within that environment. Mapping may be augmented by and/or built upon 2D and/or 3D drawings of the environment. In some embodiments these drawings may form part of the environment framework, which can then be populated by the active emissions data. The result of this process can be a 3D model of the environment, which can then be transformed into a digital twin of that environment.

In some embodiments an active mapping technology may be deployed, for example using Frequency-Modulated Continuous-Wave (FMCW) Radar to create a radar topological map of an environment. This may incorporate multiple modulation patterns, such as sawtooth, triangular, square, sine and stepped. Each of these may yield differing characteristics of the environment under evaluation. The use of differing types of modulation can enhance the identification of the boundaries of the environment and the shapes of the objects within the environment. Each type of surface, for example glass, wood, plasterboard (drywall) and other hard surfaces produces a specific signature. The same applies to softs surfaces, such as carpet, curtains, couches and the like. Given the capabilities of FMCW, this can result in an accurate representation of the environment. The use of multiple modulations provides a further refinement on these representations. Further these data sets may be passed to one or more care analytics management processors for classification and/or identification. In this manner a repository of the types of objects, wall and floor types, windows, benches, appliances and the like may be developed for use in further representations of other environments.

Such an approach can include the use of algorithmic techniques that can be deployed, for example, interferometry, which uses the relative interference patterns generated by the returns from, for example a stepped multiple frequency emission, to identify particular objects (for example furniture) and surfaces (for example windows) that are present in the environment.

The coupling of the emission based active mapping may include the use of, for example, stepped frequency radar mapping, in which the use of phase and multiple frequencies can identify the resonances of the fixtures of the environment, which can be used to reduce ambiguity. For example, a single pulse (or brief set thereof) can be used as an active sweep when such sensors are activated, to identify or confirm the location of an object or person within an environment.

A typical environment such as a domestic or care environment, has a set of inbuilt devices which can act as sensors, which can include "nightlight" motion detectors, door entry/exit triggers, window open/close triggers, smart light bulbs, smart temperature controllers/environment controllers, smart TV's, smart speakers, smartphones, other Internet of Things (IoT) devices, which includes smart appliances, such as fridges and the like. This can include any devices worn by and/or carried by a person under monitoring and/or other stakeholders. These can be integrated into the care and wellness systems, to the degree supported by their characteristics and/or configuration. Generally, such integration will be through one or more API and/or standardized messaging systems.

The environment may be profiled using acoustic emitters and receivers to determine the baseline acoustic state of that environment. This may then be used with at least one machine learning system to establish the acoustic quiescent state of an environment. This baseline can then be deployed to identity, in whole or in part, an acoustic signal within the environment, such as when a PUM walks, sits or stands, opens or closes doors, windows of drawers or undertakes other actions. The use of the background acoustic quiescent state can assist the recognition and identification of other acoustic events, which can be then stored as fingerprints, potentially in edge devices, enabling matching and comparison techniques to be deployed.

Another class of sensors that use passive sensing, such as computer vision include cameras, including the use of those with IR or other non-visible spectrum capabilities, may be used to map an environment, this can include the use of panorama features on smart phones and the like. In many cases the contents of the environment are private to the person inhabiting that environment and as such the images created in such mapping can be encrypted and stripped of any identifying features, with the functional aspects retained, in for example, a digital twin as an avatar or other representation. There are many identifying features of an environment that are not required for the effective functioning of the systems and as such these can be represented in generic form (for example books, paintings, objects etc.), represented as their functional equivalents in terms of mapping of the environment. For example, books represented as soft surfaces, or a book falling represented as an acoustic signature and the like.

In some embodiments, one or more sensors may be used to create fingerprints in one or more wavelengths, such as RF, IR, visual, acoustic and the like. This set of fingerprints, which may include one or more sensor data output, for example thermal and visual or RF and acoustic, can then form part of a pattern for an environment, for example, the quiescent state of the environment. This support of the detection and identification of variances in this state, such as for example a change in pitch of an air conditioner or generation of additional heat from an appliance, that can indicate a potential care or wellness issue for a stakeholder. Such an approach may also be used for preventive maintenance, for example where the loss of function of an appliance, such as air conditioning in a high heat zone, could cause a significant health or wellness event.

In some embodiments, one or more cameras may be deployed to capture images of the environment and the contents thereof. These cameras may include the capture of both visual and non-visual wavelengths. These cameras may be part of other devices, for example smartphones, smart TV's, smart speakers, security or other systems and/or may be specifically deployed for monitoring an environment.

In some embodiments, each of the cameras may have access to some processing capability, for example this may be part of the camera and/or host device and/or can be accessed through one or more communications capabilities. For example, a camera may have sufficient local processing to detect a change in the monitored image, for example image processing, which then may invoke one or more systems that provide further image processing such as image recognition and/or other data extraction, comparison, matching and the like capabilities.

In some embodiments, camera and other image capture sensors and devices may include one or more machine learning capabilities that provide image recognition, including video and movement, so as to be able to detect, identify, measure and/or classify various situations involving the environment and one or more stakeholders. This can include obfuscation of the image or sets thereof, such that specific distinguishing features can be recognized without full disclosure of the image detail. In this manner the privacy of the PUM or other stakeholder may be maintained whilst the data that relates specifically to the actions and/or events that have an impact on the care and wellness of the PUM are identified.

In some embodiments, cameras may be used to verify an event, such as a PUM lying on a couch, which other sensors, such as those in a smart phone, may interpret as a change in orientation that is associated with a fall. In this example the camera may provide the data that provides the context for the event and consequently can reduce false positives. In another example the image processing of the camera and any connected systems, may identify the event as a pattern matching a fall and consequently verify that wellness event. In some embodiments, such an event as a fall may be recorded by the camera and retained for access by one or more authorized stakeholders, for example paramedics and the like, as this recording may provide vital data as to how the PUM or other stakeholder fell, and the potential medical and/or health implications of that fall. In other situations, no data may be recorded, however using edge recognition the trajectory of the fall may be retained for further pattern recognition. In some embodiments, the fall may be recorded in manner that enables one or more systems to substantiate occurrence of the event and the circumstances thereof, for example to validate an insurance claim and the like.

In some cases, some of the fixtures and/or contents of the environment may be moved, removed and/or added to the environment. The separation of the fixed and variable fixtures of the environment is undertaken both in the environment framework specification and any digital twin representations of that environment.

For those objects that are significant for a person under monitoring, such as those with memory, sight, hearing, mobility or other impairment, the system may invoke one or more active sensing techniques, including emissions, beacons, cameras, haptics and the like to maintain an up to date and accurate positioning of those objects deemed essential for the well-being of the person. This can also include convenience features for a PUM, such as finding glasses, smartphones, books or other items that have been misplaced.

Figure 4:
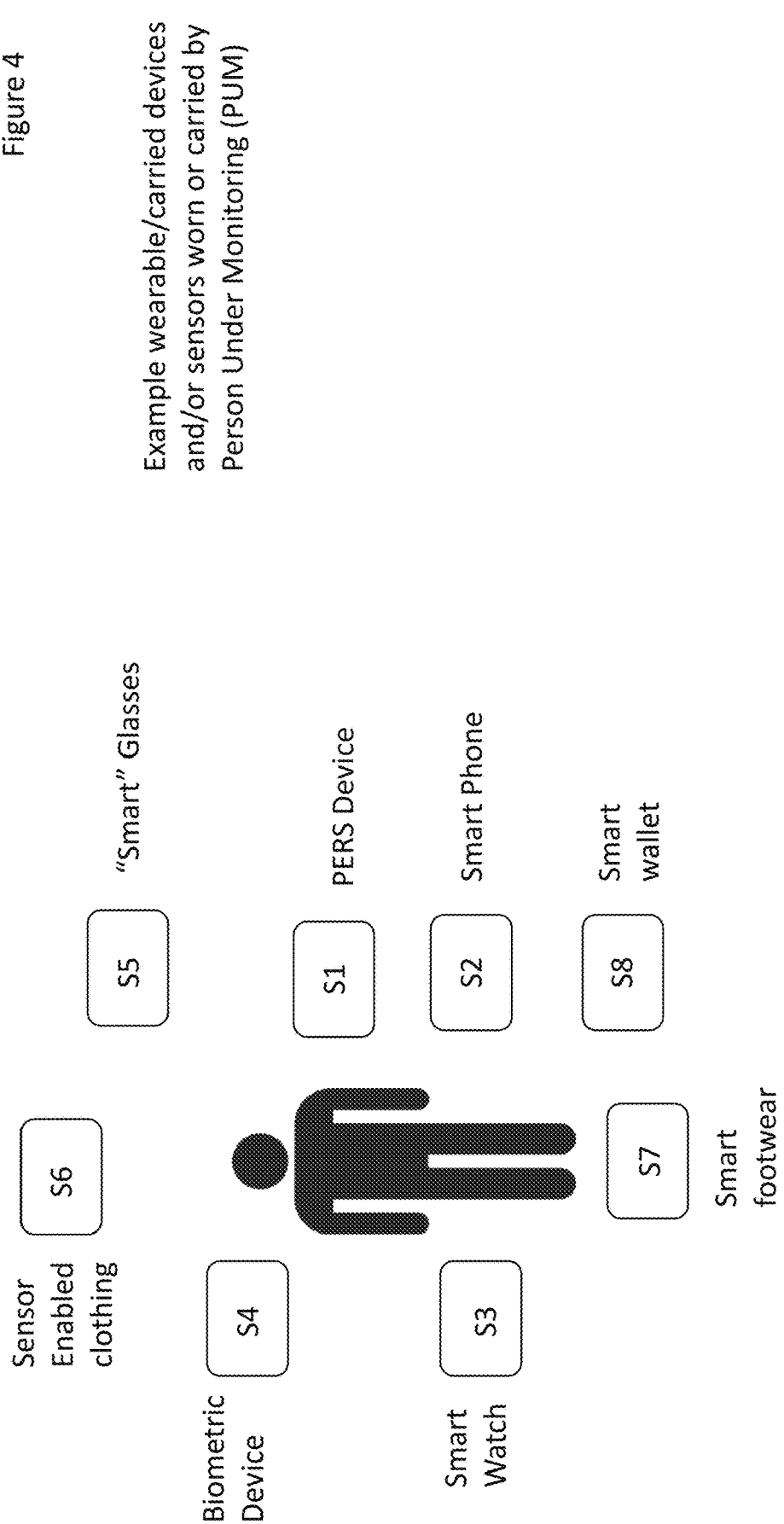
FIG. 4 illustrates a PUM with a set of attached and wearable devices.

FIG. 4 illustrates a PUM with a set of attached and wearable devices, a set of dedicated care sensors and a set of general sensors, all of which are located in the environment that the PUM is domiciled within. These sensors may be configured as edge sensors and/or may communicate with one or more care analytics management processor.

The integration of active and passive sensor data can represent a state from which any variations can be detected and such representation of state updated if and/or when required. For example, when moving furniture, installing a new appliance and the like. In some embodiments digital twins may be used as representations of the states of an environment, and as such may provide a history of the environment and the contents thereof. Such history may then be used by one or more machine learning and/or pattern recognition systems to establish any causal or correlations between care and wellness events and the content and configuration, including positioning, use, avoidance and the like in the environment.

Example Embodiment

A mobile Personal Emergency Response System (PERS) device is generally intended for elderly persons and/or for persons with physical disabilities or others with a need to request help or emergency services, for example by pushing an emergency button on the PERS device. These devices typically include an emergency button, a speaker, a microphone, and wireless communication capabilities, including for example, wireless phone functions which are used to connect the person with emergency personnel or a caretaker using voice. In some cases, a PERS device can also contain sensors and software that uses the sensors' signals to detect events such as falls, and to automatically trigger an emergency call and/or report the event to a central server and/or service when such events occur. They may also include location detection sensors, such as GPS, radio frequency triangulation, beacon readers and/or the like, which allow the PERS device, or the system that it connects with, to trigger emergency and/or other responses, for example, when the person leaves a pre-determined area (Geo-fence), when they stop moving for a long enough period of time or other location and/or movement related circumstances.

One problem with PERS devices configured with these and other sensors is that keeping all the sensors active and processing their signals most of the time, to effectively detect relevant events, can drain the devices' battery very quickly, which reduces their practicality in real-life situations. This problem can be addressed and the performance and accuracy of the PERS device's functions can be improved by applying the embodiments described herein. For example, under normal circumstances (such as the quiescent state), most sensors in a PERS device can be configured to remain dormant, except, for example an edge sensor such as an accelerometer, so that the software within the PERS device can be listening only for signals from the accelerometer that indicate movement above a pre-defined threshold, indicating that the person changed their status from a set of activities that match a normal pattern to one or more activity that exceeds one or more thresholds od that normal pattern. At this point other sensors, such as an altimeter or other height detection sensor, and/or a microphone and/or other sensors in the device can be activated. In this example, the configuration of the edge sensor, such as the accelerometer and the threshold for its data can change, such that the systems and software can switch to a different set of detection logic, creating a different configuration, appropriate for detecting the most likely events under the person's new state. Additionally, other biometric sensors may be activated, as can location detection sensors and/or geo-fence logic. In some embodiments these configuration changes may be dynamically provided to one or more sensors, including in advance to, or in response to, a change in state detected by one or more sensors, including edge sensors.

For example, a geo-fence can also trigger a new change of configuration, for example, when a "going outside" an environment is detected, the operational parameters and/or event detection logic for sensors such as an accelerometer and altimeter can be changed, in order to detect falls under the dynamics of walking outside or can be deactivated, if a "moving in a car" situation is detected, based, for example, on the combination of location changes and accelerometer data. With this approach, sensors, processing, and communications functions are only used when a detected pattern indicates that they are required, resulting in reduced power consumption. Additionally, the dynamically changing sensor configurations and detection logic allows for increased event detection accuracy.

An implication of using a PERS device as the single way of detecting risk-related events such as falls is the limited precision that results from a co-located set of sensors in a reduced size portable device. This makes it difficult to avoid false positive and false negative event situations. This can be improved by combining the PERS device's combinations of sensor configurations, data processing and detection logic with those of devices located within the same environment, but outside of the PERS device as described herein.

For example, the PERS user's home environment may be equipped with additional sensors, such as cameras, smoke detectors and/or microphones and a range of other sensors. The signals from these sensors can be combined with the PERS device's sensors' data, as well as data from other devices, such as voice recognition-enabled speakers (smart speakers and/or smart TV's and the like), as way to extend and expand the capability of a PERS system to increase effectiveness. This combination may happen within the PERS device and/or in other devices within the user's home, connected to the PERS device using a wireless communications mechanism such as Wi-Fi and/or Bluetooth, and/or at one or more systems, including those hosted on one or more remote servers. This combination can be used to determine more precisely the user's state, based on known and/or anticipated user behavioral patterns, such as typical locations and activities within the home, and the signal patterns that those activities produce in the sensor arrangement of the environment sensors in combination with the PERS device's sensors.

Some of the devices and/or system and/or system and/or server arrangements in this kind of configuration may include machine learning and/or statistical mechanisms as adaptive methods to identify patterns that indicate changes in the state of the user or the environment and to more accurately and/or dynamically select sensor configurations and/or trigger events, alarms and/or responses. Signals transmitted by the sensors in the PERS devices and the user's environment can be stored and used by one or more server for training machine learning systems and/or to supply CVDT (Care Village Digital Twins) representing a user and their environment, supporting adaptations to changes in the user's behaviors and/or in the environment. This approach supports increasing accuracy of predictions, so as to better anticipate and prepare any emergency and/or other support resources in response to changes in the detected patterns.

Figure 5:
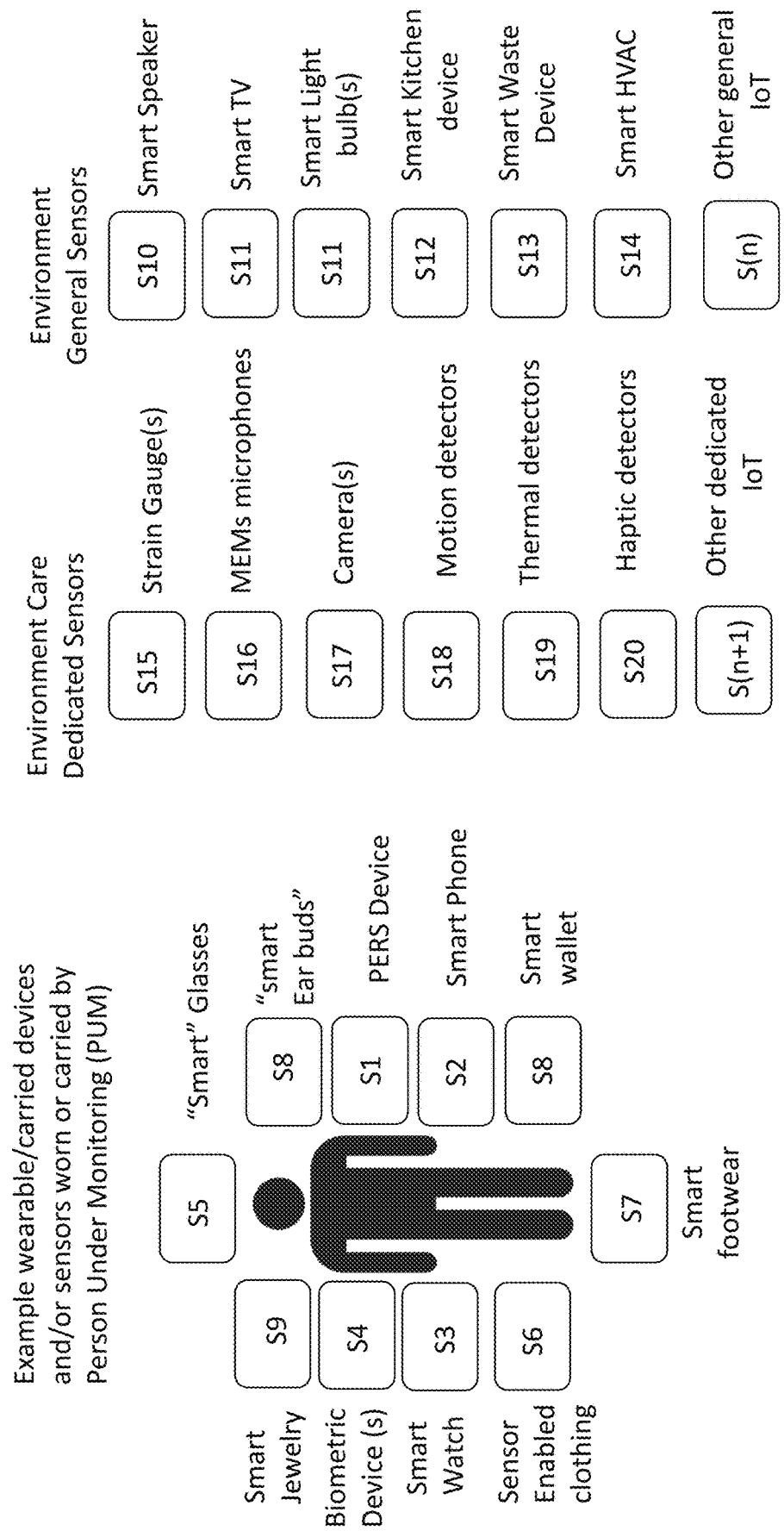
FIG. 5 illustrates a PUM (101) domiciled environment which includes one or more sets of sensors.

FIG. 5 illustrates a PUM (101) domiciled environment which includes one or more sets of sensors, including wearable, carried and/or attached sensors/devices and/or those situated in the environment, including dedicated devices and/or sensors and/or general devices that include sensors.

In some embodiments a "care VPN" may be instantiated, where specified authorized and authenticated stakeholders can access, control, configure and/or monitor one or more sensor, devices and/or systems in an environment. For example, a specialized device that provides capabilities to the sensors in an environment, may have stored an amount to data prior to a care and wellness incident, that can be made available to an EMT, paramedic, carer or other authorized stakeholder when in proximity to the PUM and the specialized device is detected, determined, represented or enabled. For example, this can be the case where the PUM is undergoing a care incident and, for example, a specialist for that type of incident is made aware of the situation.

In some embodiments, a "care VPN" may be instantiated between the specialized device and one or more stakeholders enabling the data being managed by such device, including data stored by that specialized devices elastic repository to be available to one or more authorized and authenticated stakeholders. In some embodiments this may include the use of secure tokens for such access.

The previous description of the embodiments is provided to enable any person skilled in the art to practice the disclosure. Thus, the present disclosure is not intended to be limited to the embodiments shown herein, but is to be accorded the widest scope consistent with the principles and features disclosed herein.

Sensor Types

In some embodiments, there may be one or more specialized sensors that are designed to detect specific events, including those that are specifically care and wellness related and/or provide indications of variations in care conditions, of one or more person in one or more environment. These sensors individually or in aggregate in any arrangement may provide data to one or more systems to establish one or more patterns of a stakeholders domiciled in an environment and/or an environment itself.

In some embodiments sets of sensors may be integrated and deployed within an environment in manner that is designed to ensure that the behaviors of a stakeholder, including a PUM, are effectively monitored in support of the care and wellness of that PUM. Each environment may incorporate different arrangement soi of sensors so as to provide sufficient coverage of the environment, to establish and monitor patterns of behavior therein. In some embodiments, various combinations of sensors, including those that are worn or carried by a PUM, are deployed so as to establish the state of the environment and/or the stakeholders thereof in support of one or more patterns being monitored. Some examples of such sensor and/or devices are described herein.

Strain Gauge

Strain gauges can be used to detect a range of variations of the degree of strain under which a surface, to which the strain gauge is attached, is subjected. For example, if a strain gauge is attached to a floor, and there is an impact from a falling object, pet or person, the strain gauge can detect and measure such an impact.

Strain gauge sensors may be hard wired and/or wirelessly connected to one or more systems that monitor their operations. The sensitivity of the strain gauge may be varied through electronic and/or mechanical methods and/or one or more signal processing and/or data processing systems. In many circumstances the strain gauge will have an electrical connection that enables the measurement of impacts detected by the strain gauge. As temperature can affect the sensitivity of the gauge, this may also be measured and can be used to configure the measurements from the strain gauge.

One aspect of this approach is the measurement of the various impacts, both intentional and unintentional, such as those caused by footfall of a the PUM, or other Stakeholder walking in an environment or from a fall, trip or other misadventure. The strain gauge may also detect and measure the impact of a pet, including for example a cat landing on a surface, or a dog lying down and the like.

Strain gauges may be deployed in an arrangement, for example at the corners of a room, such that the measurement of an impact can be detected by each of the gauges, and will differ in relation to the location of the impact within the environment. When the strain gauges are connected to one or more systems, these multiple data sets may be combined to enable evaluation of the data, for example to determine the velocity, acceleration, mass, direction, location and/or other characteristics of the impact. This can provide, for example, a pattern of a PUM walking within an environment, a pet traversing a room and/or an impact that indicates a care or wellness event. In some embodiments, such data generated by one or more strain gauges may be provided to one or more machine learning, pattern recognition, matching or other analytic and/or evaluation systems, to determine, in whole or in part, patterns of movement and/or other impact occurrences within an environment.

Strain gauges may be attached to or integrated within the surfaces they are monitoring. For example, a strain gauge may be attached to a wooden floor, or other hard surface with high rigidity and/or may be woven into softer materials, such as carpets and the like. In the example of the carpet, the pattern of strain gauges may be such that they form one large gauge, a number of independent gauges, or sets of gauges in any arrangement.

In some embodiments a strain gauge or set thereof may form part of a sensor. For example, the sensor may include communications, processing, memory and/or other elements. For example, a sensor comprising one or more strain gauges may have a processing capability sufficient to determine an impact or set thereof, that can be pattern matched to a previously identified impact or set thereof, such that an accurate identification of the pattern is achieved. This identification may then be transmitted to another system, sensor and/or other authorized entity, for example in the form of a token. This can include the sensor incorporating a set of tokens representing different occurrences, including the state of the environment, such as the quiescent state. The token may include one or more metrics, such as the degree to which an occurrence matches a pattern, which may be, for example, expressed as a degree of confidence.

In some embodiments, a set of strain gauges may be used as a network, where machine learning may be used to evaluate the incoming signals, some of which may be of low intensity, and using, for example, a neural network or other undirected learning approach, one or more signals may be detected.

In some embodiments, a strain gauge can be designed in the form of an antennae to match either of typical Wi-Fi and/or Bluetooth frequencies such as 2.4 Ghz, 5 Ghz or 6 Ghz. Each of these deployed strain gauges can provide a signal to a central server, when the antenna is energized through the absorption of the transmitted RF energy. For example, where the output of the strain gauge is within a range determined as the quiescent state of the strain gauge, this would represent no measurable activity. For example, an FMCW radar may be used to energize the strain gauges, where those strain gauges are formatted in manner that is compatible for an antennae for the FMCW radar signal being transmitted, for example from smart light bulbs. In both these examples, this negates the need for the strain gauges to be wired as they are energized by the RF, and as such the monitoring system, operating at the same frequency can detect the variations in strain gauge output as they experience the changes in measurement caused by one or more impacts.

If an event occurs such as a fall, where the signal from the strain gauge is disrupted, this data is passed to one or more central servers and/or edge devices, including sensors, and is used to trigger one or more events, including responses, alerts, and/or sequences thereof.

The pattern of movements typical of a person in an environment is also captured by the strain gauge, in that footfall of persons will also create patterns in the quiescent state, which although of less magnitude than that of a fall, are still able to be determined through the use of, for example, machine learning techniques. Such movements form patterns that can then be incorporated into behavior or other wider patterns of activity for a PUM. For example, if a PUM regularly traverses an environment from bed to bathroom, this when correlated to time can indicate the use of those facilities.

For example, a learning phase for the machine learning is the recordation of the steady state of the strain gauges with at least one source of transmission of a suitable frequency with no persons present. In this manner a baseline is established for the environment. The system then is set into a second learning stage where the person uses the environment and the footfall of that person is recorded as a further "natural" state of the relationship between the person and their environment. This can then form part of the quiescent state of the environment with the PUM present and undertaking their natural and normal activities, from which any deviations can be detected.

Using machine learning to establish a baseline pattern for the relationship between the environment and the person can establish the normal behavior characteristics from which events and alerts, such as a fall, may be determined The strain gauge can be attached directly to any surface, predominately the floor of an environment to detect a fall. This connection may be direct or indirect, for example the stain gauge may be attached to furniture or other objects and devices connected to the surface of interest. This can include both hard and soft surfaces.

Windows and Surfaces

Any habitable environment will have one or more window, with at least one surface facing and exposed to the inside of the environment. This surface can be used for a number of sensor placements and can be incorporated into the capabilities of one or more sensors.

For example, a window may be used as a microphone though the attachment of a suitable sensor, such as a MEMS microphone or other suitable acoustic sensing device. In this manner the windows in an environment can capture acoustic information in the environment.

This detection may include the use of voice recognition techniques, determined by, for example, the identification of key phrases, such as "help," "fall," "assist" or other terms that a stakeholder, such as a PUM, may provide the system during a learning phase. This learning phase may be structured, in that for example, the PUM moves around the environment repeating specific words or phrases, which are designated as trigger phrases that can be detected by one or more sensors, including any devices that incorporate a microphone, and can be recognized by one or more systems, which can then invoke one or more responses.

For example, such acoustic capture sensors, such as MEMS microphones or other microphones, such as those included in smart speakers, smart TV's, smart watches, smart phones, PERS and/or other sensors, devices and/or systems may be used to detect and identify inflections in one or more speech patterns of one or more stakeholders. For example, this can include detection of stress, anger, frustration and/or other speech related characteristics, including repeated or specific phrases and the like. Such an approach can also detect other sounds, such as those emitted by a stakeholder when, for example, they have experienced a fall or other wellness and/or care related event. This can include sounds that represent the experiencing of pain or discomfort to a greater or lesser degree, for example moaning, screaming, crying, cursing and the like.

These and any other microphones may have sets of filters applied, for example to attenuate or emphasize speech, have high, low or bandpass fileting applied so as to detect specific occurrences, for example, sounds representing and/or associated with a fall, collision, breaking of furniture or objects and the like. In some embodiments, specific sets of filters, using for example DSP, may be applied, for example, in the quiescent monitoring stage, or when an event or trigger is detected, which This may include beam forming so as to directionally focus the microphones towards the detected, directly and indirectly, sound source of interest. This can be invoked, for example by another sensor, where the first sensor detects a change in state of sufficient magnitude, for example an increase in acceleration, change in height or other attribute as detected by a worn device, for example a PERS, and sends directly or through or in conjunction with a service, a message to a second sensor for confirmation of the detected event.

Filtering applied to the microphones may be changed dynamically in response to an event, directly or through another device, so as to focus on the frequency range, amplitude or other characteristics associated with speech or other utterances from a person, especially in relation to the specific words or phrases that have been stored previously by the one or more systems and/or in response to detection of sounds that are indicative of an impact, fall or other occurrence that affects the care or wellness of a PUM.

The use of other flat surfaces for the mounting of microphones, such as MEMS microphones, can also be used. Windows, given the characteristics of glass are particularly suitable for capture of acoustic signals, however other materials such as plastics, wood, and the like may be used. Many environments have expanses of flat surfaces, which can be used to capture acoustic data. Often the larger surface areas can be used to capture longer wavelengths, such as those of low frequency acoustic events, such as those created when a PUM or other stakeholders falls or impacts a surface.

For example, a MEMS microphone may be deployed on a hard surface, potentially in combination with a strain gauge as a detector of impacts. In some embodiments, these mems microphones can be attached to hard surfaces, such as walls, windows, floors or the like, and as such can detect acoustic vibrations and disturbances representing changes in state of the quiescent or other state of the environment.

The use of MEMS microphones or other microphones within the environment can be used to track acoustic events, directly and indirectly. For example, a MEMS microphone, or other acoustic sensor, on or near bathroom plumbing can indicate the use of bathroom functions without disturbing the privacy of the person using the bathroom.

The relative positioning of these microphones and/or other acoustic sensors, can provide differing signals, which when processed with appropriate digital signal processing techniques, such as Fast Fourier Transform (FFT), phase shift analysis, filtering, Digital Signal Processing (DSP) and the like, can provide data sets that separately and/or in other arrangements can inform as to the activity within the environment. For example, the location of a person in a multi room environment, the dwell time in a specific location, such as bedroom, bathroom, kitchen, when a person is moving in an environment and the like.

Acoustic fingerprinting of an environment, in part or in whole, may be accomplished using appropriate acoustic transmitter and such MEMS or other types of microphones in any arrangement. However, in most circumstances there will be positions in the environment that are preferable for the location of such devices. For example, ceilings, hard surfaces such as walls in corridors and the like.

The use of sets of MEMS or other microphones within an environment can be arranged such that microphones provide sufficient coverage of an environment so as to create an acoustic fingerprint of that environment, in whole or in part. This fingerprint can contribute to the state of the environment and become part of the environment specifications, including as part of the quiescent state of the environment. The outputs of each microphone may be evaluated individually and/or in aggregate in any arrangement to determine one or more patterns of activity, movement and/or behaviors of a stakeholder within an environment. This can include establishing acoustic fingerprints for various activities and behaviors, such as traversing a corridor or room and the like such that the state of the stakeholder activity within an environment can be determined, generally in relation to one or more patterns.

In some embodiments placements may be such that the microphones are positioned so as to create geometric relationships, such as on opposing walls, forming triangles or other shapes. These geometric relationships may then be used by, for example, a care analytics management processor as part of the signal analysis. For example, the phase, amplitude, reflections, temporal and/or frequency relationships may inform the care analytics management processors evaluation.

Thermal Sensing

In some embodiments, the environment sensing can include the use of thermal sensors to establish the sources of thermal radiation within an environment. This can include an initial survey without any PUM or other stakeholder present, which can then form the baseline for further sensing by such thermal sensors to establish the location of a PUM in such an environment.

Thermal imaging and/or temperature-derived data may be used to establish the presence of a person in a part of an environment and/or establish the condition of the person and of the environment itself. Infrared sensors can be used to determine the relative differing temperatures within an environment, and may be combined with visual cameras to determine the source of such temperature differentials. For example, in adverse weather conditions, the thermal sensors may provide data that indicates the temperature within an environment is likely to cause or influence a care or wellness event. For example, if the external temperature is excessively low or high, for example during a winter storm or summer heatwave, the temperature of the environment may become such that the PUM is exposed to excessive cold or heat respectively. This thermal sensor data can be used to activate HVAC or other climate control systems, however in some circumstances these systems may not be able to provide sufficient mitigation of the external conditions. In this situation one or more alerts or events may be generated by the care village systems, including for example, alerting carer, neighbors, friends and/or family to this situation. This can also include providing the PUM with a message, for example through a smart speaker to vary their clothing or in other ways mitigate the effects of the external conditions. This can be particularly important in relation to the memory impaired.

The use of thermal sensing can include identification of environmental activities, such as use of cooking appliances, running of showers or baths, heating and cooling and the like. For example, such thermal sensor data may be used in conjunction with other sensor data to verify and validate that a PUM behavior pattern is consistent or that there is a variation from that pattern.

The use of thermal sensors may also assist in determining the movement of a PUM, including for example their presence in a bed, traversal between rooms in an environment and the like.

Thermal sensors may also provide data that indicates the overall temperature of an environment, for example the temperature during weather events. For example, if there is a high external temperature, the sensors data may indicate the environment internal temperature is approaching a threshold which can cause a PUM to experience a wellness event, such as heat fatigue and the like.

Motion Detectors

Many environments have motion detectors and/or incorporate devices that include such functionality. For example, most home alarm systems incorporate one or more motion sensors. The integration of a motion detection function into a sensor set can act as an edge device to trigger other sensors in that environment. For example, a motion detection may trigger a camera and/or other device, for example, a smart speaker may be activated and/or may emit a message or query, such as "hello", "are you ok", a beep or other audible announcement.

Motion detectors may also be used in a variety of locations so as to inform one or more sensors, devices or systems of the presence of a PUM or stakeholder, and in some cases pets, robots or other non-human presence. This can be used, for example to determine whether a PUM has entered or exited a room or other space.

In some embodiments, motion detectors can form part of a set of sensors and act as edge trigger devices to alert other sensors, devices and/or systems to the presence of a PUM or other stakeholder. This is particularly useful when these other devices have power requirements which require conservation of those resources, such that they are only active when triggered. This can also be the case when the motion detector ceases to detect any movement.

In some embodiments motion detectors may be used to vary the configuration of one or more sensors, devices and or systems. This can include configuration for enhanced or extended sensor capabilities, for example turning on a camera or activating an active sensor. Such configurations may also be used to reduce or constrain the operations of a sensor, device and/or system, for example in support of privacy of a PUM and/or other stakeholder.

In some embodiments, motion capture may be detected from one or more image capture systems, for example camera's, where the camera has sufficient image recognition capabilities to identify changes in the image being monitored.

Motion detection patterns may form part of one or more behavior patterns and may indicate variance from a pattern by a PUM or other stakeholder. For example, if the motion detectors indicate that a PUM now has a different set of movements, for example a repetitive use of an appliance in a short time period, this could indicate a change in state of the PUM short term memory indicating further memory impairment.

For example, a motion detector, in combination with a strain gauge and/or a PERS or other wearable or carried device, may identify a change in the PUM's movement patterns, for example where a hip, knee or other physical aspect is deteriorating and causing them to have a change in their mobility. In some embodiments, the motion. Detection may act to configure the strain gauge, PERS and/or other sensors, devices and/or systems to capture and/or measure the movement of the PUM. This movement may then be evaluated, and determined to be within the thresholds of an operating pattern or being sufficiently varied from that pattern so as to indicate a change in the PUM mobility.

Smart Light Bulbs

The emergence and availability of smart light bulbs provide another sensing capability, in that such devices incorporate radar technologies which can determine certain biometric functions, such as heart rate, body temperature and the like. In some embodiments such devices may be integrated into an environment so as to provide environment lighting, which can be integrated into one or more environment sensing systems, to provide care and wellness benefits to the one or more stakeholders occupying the environment.

One type of technology that is employed by such light bulbs uses FMCW (Frequency-Modulated Continuous Wave) radar in the 2.4 Ghz range. In some embodiments, a set of smart light bulbs may comprise an FMCW mesh. For example, if each room in a multi room environment has one or more smart light bulbs, biometric data for a PUM may be tracked from room to room in a seamless manner.

One aspect of the use of smart light bulbs, is the ability of these to track sleep patterns in a non-invasive manner. The data from such devices can then be integrated into one or more patterns for a stakeholder providing a comprehensive data set supporting the evaluation of their wellness situation. This is particularly the case where such data is integrated into one or more digital twins, which can then be used to inform one or more predictive systems for the identification of changes in the patterns of behavior that indicate a potential wellness or care event.

In some embodiments, FMCW RADAR may be used in specifically designed devices for the tracking of care and wellness data of a stakeholder. Such devices may be mounted within an environment and be configured to detect and identify breathing and/or other care and wellness patterns of a PUM.

Haptics

In some embodiments haptic detectors may be employed, both to provide a PUM with a method of communication with the system and/or stakeholders and/or as a sensing method to determine the actions of a PUM. For example, a surface that is likely to be grasped as a person tries to regain their footing or avoid a fall, such as a banister, may have a haptic detector which can sense such an activity.

Haptics may also be worn as additions to clothing and/or as part of clothing, for both monitoring and providing communications. For example, a small pad may be attached to or integrated into clothing, such that applying touch to that pad can create one or more messages for communications to one or more sensors, devices and/or systems. For example, differing touches, such as specific single finger, multiple fingers, thumb, palm any combination thereof may produce different messages. This can include emergency calls to 911 or other emergency services, for example after a fall or mishap, where the stakeholder is unable to access another device but can touch the pad, providing a haptic signal.

In some embodiments, the pad may be worn on the forearm, for example near the wrist, and may include a power source, including those that generate energy from movement, one or more communications capability and one or more identifier. This can include specific serialized indicia and/or antennae that can be recognized by one or more sensor, device and/or system, such as a QR code or other type of barcode, electronic identifier and the like.

This can enable the wearer to be tracked in their movement, particularly in terms of entering or exiting an environment or area within that environment. Such a pad can include one or more biometric sensors and/or alignment indicia, either of which may be used for detection by one or more sensors, devices and/or systems of a stakeholder changing their alignment within the environment. For example, if a PUM moves form a standing to sitting or lying position.

In some embodiments, the haptic sensors may be mounted in the environment so as to provide a communications capability for a PUM or other stakeholder who may not have another way to communicate their situation. For example, in a bath the pad may be on the side of the tub or easily reachable from within the tub, such that if a PUM is having a care or wellness event, they may use the haptic pad to communicate with one or more sensors, devices and/or systems to call for assistance. Other potential locations may include stair cases, areas adjacent to floors, where there is a high probability of a fall occurring and the like.

In some embodiments a haptic surface or pad may be connected to one or more other sensors, devices and/or systems. Such surfaces and/or pads may be configured to act as, for example mouse pads to control one or more computing devices, remote controls for appliances, such as Smart TV's, Audio systems, HVAC, stoves and ovens or other appliances. In some embodiments this can include a haptic interface device that receives input from the haptic device and then translates these communications into commands and configurations for the one or more target devices and/or appliances. This can include communications that create command and configuration sets for multiple devices and/or appliances, for example, either simultaneously or in a temporally ordered arrangement.

In another example, the haptic surface may be embodied, for example, into a yoga mat or other functional surface, including for example a bed comforter, shower mat, bath mat and the like. In this example, the haptic surface may act as both sensor and communications system, with differing areas of the surface undertaking either or both of these functions. This can include the configuration of the surface from one function to another, either directly or remotely. For example, a PUM may put their hand on a haptic pad, which will then configure a bath for their specific needs.

In some embodiments, haptic sensors could be deployed such that when a PUM grabs a surface, such as a door handle, stair rail, fridge door and the like, the haptic sensor may create a data set for the strength the PUM used. This data can then form part of the behavior pattern for the PUM, potentially indicating variance in the applied strength, which can indicate care and/or wellness issues. This can also include walkers, zimmer frames, canes or other mobility assistance devices.

The integration of a range of haptic sensors and/or control surfaces in an environment can provide data sets that can be integrated into one or more behavior patterns.

In some embodiments, where the use of a camera is considered as invasive, a CCD type of detector may be used, with edge determination algorithms that can distinguish the shape of a PUM to the degree necessary to establish their orientation, for example standing, sitting, lying in relation to the environment. In this manner such sensors may be deployed to bathrooms and the like, where many falls do occur, without compromising the privacy of the PUM. In some embodiments, such CCD may capture full resolution video, which is stored for the time period that the PUM is using the bathroom or other facilities, however this data is only available to one or more authorized stakeholders in the event of an emergency, such as a fall, where it is determined such data is vital to the care of the PUM. For example, if a PUM falls and hits their head on a bathtub, such data may be essential in caring for the PUM. Even in this example the may be blurring or other privacy features that can still provide the pertinent data, whilst protecting the privacy of the PUM.

Wearable, Carried and Attached Devices

There are a wide range of devices, which include sensors of various types, that a PUM may carry, wear or attach to themselves. Certain wearable devices may also be attached to other stakeholders and/or to pets that are domiciled in the same environment. These can include devices such as Personal Emergency Response devices, which are intend to identify critical care conditions and alert designated stakeholders as to the occurrence of such events. There are also a plethora of devices, such as smart phones, smart watches, fitness trackers, smart wallets, biometric devices (including biometric headbands, EEG/ECG sensors and like), sensor enabled clothing, smart glasses, smart footwear, smart jewelry, smart ear buds and the like that can be integrated into a sensor enabled environment, so as to provide data sets that can be integrated into one or more patterns, for an environment, PUM and/or other stakeholder.

The trend of integration of electronics, sensors and more recently haptics into wearable devices enables multiple sensors to be integrated into the care village systems. These range from those having a specialized function, such as blood pressure monitor, to those that have sets of sensors, such as fitness trackers, smart watches and the like. This includes those sensors that are integrated into clothing or other wearable materials.

Many of these devices may be designated as edge devices, in that they provide the initial data set that initiates an event, alert and/or triggers other sensors, devices and/or systems. The proximity of these sensors and devices to the PUM, ensures that the data they provide is accurate, however, there may be circumstances where the context of the data reveals a more accurate perspective on an occurrence. This is particularly the case with false positives. For example, if a device detects a sharp change in direction, velocity and acceleration, for example, as detected by a smart watch, this may be determined as a fall, where in fact the PUM tripped and righted themselves. The triggering of other sensors, for example, a camera and/or the non-triggering of further sensors, for example a strain gauge for detecting impact, can provide context of that occurrence, reducing false positives.

It is anticipated that the integration of sensors and devices into wearable clothing or materials will continue, and as such the care village systems will integrate these sensors and devices into the environment sensing systems. This integration can include receiving data sets from these sensors and devices as well as configuring such devices in light of circumstances. For example, they may be switched off during certain activities, have their sensitivity increased or decreased, have their cached data set extended, recorded ort erased and the like.

In some embodiments, a PUM may have one or more movement aids, such as a cane, zimmer frame and or the like. These movement aids may be fitted with one or more sensors, including haptics, that can be integrated into the environment sensing. These sensors may contribute to the one or more patterns and may also be configured as edge sensors for the detection of care and wellness events. In some embodiments these movement aids may incorporate other devices for the mitigation of falls or other wellness events. In some embodiments, these may be considered as smart movement devices, where the potential range of sensors can include, for example, motion detection (accelerometer, gyroscope, altitude/barometric pressure), haptics, impact detectors, cameras, RADAR/LIDAR and the like. There may be some of these devices that are equipped to have other mobile devices, such as PERS, smart phones and the like attached to and/or integrated into the movement devices.

In some embodiments shoes or other footwear may include one or more sensors which can communicate with, for example, another wearable device, sensors, devices and/or systems that are part of the environment sensing and the like. For example, a pressure sensor may measure the pressure of a PUM's foot on the shoe, or insert into that shoe, so as to establish the baseline for normal mobility of that person. This data may form part of a pattern for that PUM, and when such measurements fall outside that pattern, the sensor may issue an alert to one or more other sensors, devices and/or systems. For example, if the PUM trips, but does not fall, these missteps may be evaluated to establish any pattern, for example an increase in missteps which can predict an increased likelihood of a fall. This data may also be used to evaluate the environment from the perspective of removing impediments that may lead to or increase the chance of a fall, thus benefiting the care and wellbeing of the PUM.

In some embodiments, such footwear may include integration with other smart clothing and wearables, which may include one or more small or micro airbags that can deploy when a fall is detected by the footwear and/or other sensors.

Emission Technologies

The range of devices that incorporate RADAR/LIDAR and other RF, Visual and line of sight emissions is expanding, in part due to the development of autonomous and semi-autonomous devices, including vehicles. These emission-based sensors may be deployed within a care village environment to, for example, identify and locate stakeholders, other sensors, devices, environment furniture and fixtures and the like. For example, a PERS or similar device worn on and/or attached to clothing may provide forward facing data as to changes in inclination of a surface, for example on a walking track, or stairs and the like. In another example, the sensors may provide data as to the distance of a wall or other boundary.

In some embodiments, IR technologies may be deployed to provide night vision, through for example IR capable cameras mounted within an environment and a portable device capable of displaying the image captured by such camera. For example, this may be used when there is a power loss at night, and the stakeholder may then receive an image of the environment where, for example they have been requested to move to an exit or other place of safety.

FIG. 4 illustrates examples of such devices and FIG. 5 extends those examples as well as illustrating the dedicated care sensors and the general devices and sensors that may populate and/or be embedded into the domiciled environment of a PUM.

Environmental Sensing

In many environments, smoke, $CO_2$, Carbon monoxide and other environmental sensors are deployed for the safety and well-being of a stakeholder within such an environment. These sensors, and other gas, atmosphere and other environmental sensors can produce data indicating the quality of the atmosphere within an environment. In some embodiments, multi-purpose devices such as smartphones, smart watches can include such sensors, as can specialist devices intended to monitor the atmospheric conditions within an environment. In common with other specialist, single and/or multi-function devices, the data generated by these sensors may be incorporated into the care village monitoring systems. Such data may form patterns that can be included within an overall monitoring pattern for an environment and one or more stakeholders.

In some embodiments, data from these sensors may be used to activate other sensors to verify the occurrence of an event and/or contribute to a data set that indicates a wellness or care event is likely to occur. These sensors may also provide data that indicates the presence of a PUM and/or other stakeholder in such an environment.

Robots

In many circumstances there may be one or more robotic device that operates within an environment, for example, vacuum or other surface cleaners. As the development of autonomous and semi-autonomous devices accelerates, the deployment of robotic devices is likely to increase.

In some embodiments there may be specialized robotic devices that are designed to support care and wellness of a PUM, where each of these devices has a set of integrated sensors, which can be configured to interoperate with sensors, devices and/or systems of an environment. For example, if an environment has an outside area, such as the back yard of a house, a drone with integrated sensors may be deployed when a PUM enters that area. Such drone may incorporate geo fencing, such that it stays within a designated area at a predetermined height. The drone may have a fixed charging station that is attached to the environment.

In some embodiments the drone may be sufficiently small as to be mounted, for example on the clothing of a PUM, for example the shoulder, and may be dispatched by the PUM or another stakeholder, sensors, device or system, to survey an area the PUM is entering, or provide line of sight or other communications capabilities to the PUM. In this example, the clothing worn by the PUM may include a charging and docking capability for the drone. This can include latching and other connection types.

In some embodiments there may be a robot designated as a finder. This device has mobility capabilities, for example, wheeled, tracked and/or limbed and the like that is capable of traversing an environment and includes a set of sensors and communications capabilities. The finder can be used to find a specific stakeholder, in most cases the PUM. For example, the finder may identify the location of a PERS, smart watch, smart phone or other device, which is being worn or carried by the PUM and move to that location. The finder may be equipped with a range of sensors, including those that can be accessed by emergency response or other care and well being teams. For example, the finder may include camera, FMCW, microphones, speakers and the like, sufficient to enable the team to evaluate the condition of a PUM. For example, if a PUM has fallen or injured themselves in a situation where there the sensors, devices and/or systems are insufficient to evaluate the condition of the PUM and/or do not have the communications capabilities for a remote team to communicate with the PUM, then the finder can provide those capabilities.

The sensors may provide data sets that indicate the breathing, heart rate and other biometric information that can be communicated to one or more authorized and authenticated stakeholders, for example a medical or emergency response team and the like. This can include the ability of that team to speak with the PUM, so as to be able to reassure the PUM and gain further details from the PUM and/or other stakeholders on the PUM's condition.

In some embodiments, the finder may include some assistance capabilities, such as being able to lift the head or limb of a PUM. Such capability may be remotely controlled.

In some embodiments there may be robots, such as those that operate on floors, that include sensors for detection of vibrations on the floor. This data may then be used in the identification and/or detection of patterns of vibration of one or more stakeholders and may be incorporated into one or more patterns. In some embodiments, there may be room and/or furniture and/or fixture specific sensors, for example pressure sensors installed on, under and/or within a bed to detect the presence and/or movement of a stakeholder. A similar approach may be employed for couches, chairs, sofas or other furniture intended for sitting, sleeping or resting. The data sets form such sensors may be incorporated into one or more patterns of behavior for a stakeholder, including a PUM.

Pets

In many environments, the PUM may have one or more pets as companions. As most all pets have some form of collar or can be fitted with a small portable sensor or device, these can be co-opted into the environment sensing systems for the care and wellness of a PUM.

Environment State

In some embodiments, each device equipped with one or more sensors can have one or more states that are in part or in whole determined by the configuration of that device and/or sensor. For example, if a device that includes a sensor is generating data, the state of the device and/or sensor may be determined by one or more other sensor, device and/or system that has configured that device independently and/or in collaboration with other sensors, devices and/or systems.

For example, a device sensing an at rest environment, for example a room with no person present, and no activity in that room, may represent the state of that environment as quiescent. This can include when the sensor is active, however the state of the device is quiescent. For example, a camera or microphone may be receiving photons and acoustic vibrations respectively, however the state of the device is quiescent in that neither of these inputs represent an occurrence that s=changes the state of the device.

This approach can include the state of the sensor, device and/or system is determined, in whole or in part, by patterns of data that represent the state of the environment and/or the stakeholders therein. For example, if a person is undertaking part of their normal behavior pattern, determined in whole or in part by the one or more sensors deployed in an environment, and the data set is compliant to a specific pattern, including and any thresholds, variations and/or variances that are part of that pattern, then the environment and sensors, devices and systems can represent a quiescent state of that pattern.

An environment may have a number of devices therein, each of which has one or more sensor, and in the case where the environment has no person present and no activity operating, this combination of device states represents the quiescent state of the environment as represented by the aggregation of each sensor state. Such a state may change over time, for example during the course of a day/night cycle and over the course of the seasons of the year where the environment is situated.

In some embodiments, external information sources such as weather monitoring and the like may be used to predict and/or verify these changes, which can then be updated by the data sets provided by the devices and their sensing capabilities.

Environments may also have a set of states that are determined by their purpose, for example a bathroom, kitchen, laundry and the like. Such specialized environments have a quiescent state and specific activated states, where the person (s) occupying that environment can have a dwell time and specific activities associated with the purpose of those specialized environments.

For example, these activated states may be specified, either by the system and/or by devices and/or sensors activated by the one or more actions of a person in that environment. These activated states may be quantized so as to form a set of activities that have relationships with the environment and the one or more person(s), such that the behavior patterns may be determined, monitored and/or evaluated.

Figure 7:
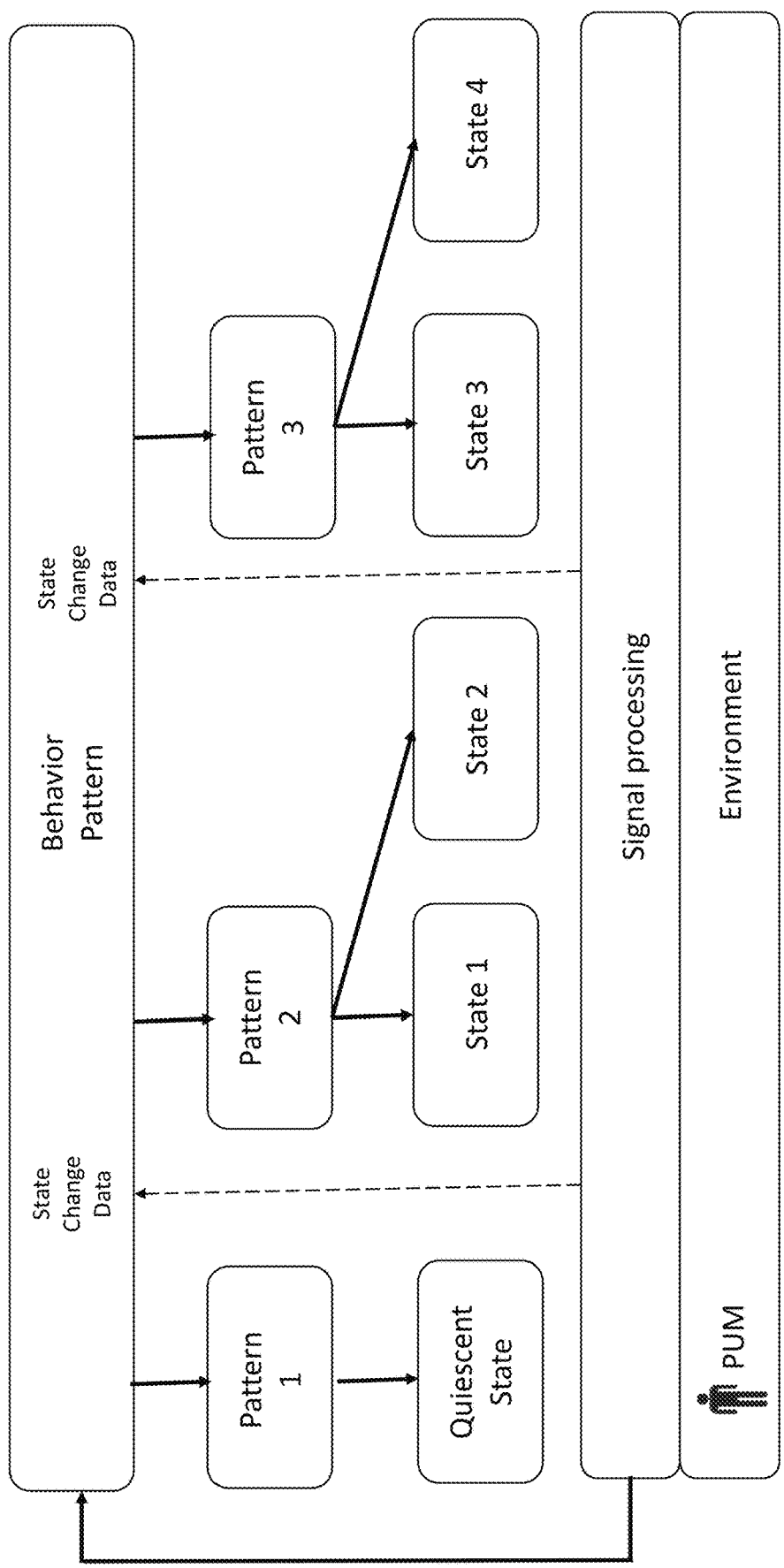
FIG. 7 illustrates the management of state by a care analytics management processor (105) for an environment (102) with a PUM (101.

FIG. 7 illustrates the management of state by a care analytics management processor (105) for an environment (102) with a PUM (101), where date provided by one or more sensor indicates and/or is identified as data representing a state change, which is correlated to one or more behavior pattern, where each behavior pattern (107, 127, 137) can include a set of patterns, each of which may have multiple states, which are referenced to the initial quiescent state (109) for that behavior pattern.

Environment Patterns

One or more sensor and/or device can be used to establish a quiescent state of an environment. This state can then be used, including in combination with one or more machine learning determined patterns of behaviors of one or more stakeholders, including a PUM, to evaluate the environment being monitored. In some embodiments, this state can be monitored and recorded in a manner whereby the data from the sensors is not considered and/or evaluated by the devices and/or systems monitoring that environment unless and until an event, represented by one or more sets of data, that changes the state of the environment is detected by one or more sensor, devices and/or systems. This includes a set of techniques, involving configuration of at least one or more sensor, such that data from that sensor is evaluated and/or analyzed to establish a transition from a steady state, for example one that is quiescent, to a state where the configuration of one or more sensors, devices and/or systems is made active. The initial sensor that detected the event, is designated an edge sensor, and may directly or indirectly initiate changes in the configurations of other sensors, devices and/or systems that escalate the monitoring of the environment in line with change in state of the environment. This can include deployment of one or more patterns in such monitoring systems to which incoming data sets may be compared.

In some embodiments, this can include heat maps of the use of an environment by a PUM or other stakeholder, which can form part of a pattern. For example, the motion of a PUM or stakeholder as they traverse an environment may form part of such a pattern and may then form the basis for the configuration of one or more sensors, including edge sensors, as a person moves within an environment.

In a steady state situation, the monitoring focus may be broad and the data sets collected from any sensors may be sparse. This collection may involve random sampling of the data set of a set of devices, based on variables such as time, including time of day, location within an environment of a person, patterns of behavior of that person and the like.

These steady states may, in part, be determined by patterns of care and wellness related behaviors, described herein as a plateau, where a person under care has a particular health situation and as such their specific health information, including their behaviors indicates the relative health condition of that person in relation to the health care plateau. For example, if a PUM has a consistent condition, such as arthritis, breathing difficulties, mobility difficulties and the like, these are represented by behavior patterns which are consistent within that pattern, and as such are described as a plateau. These health care plateau may be, in part defined through patterns of behavior, health data sets, health professional diagnosis, historical analysis and the like including the use of machine learning in any arrangement.

In some embodiments, sensors, devices and/or systems monitoring these patterns can be used to detect variations in the data set that represent a deviation from this plateau, and such a change in the state of the PUM and their environment. These deviations can then be used to create one or more alerts, events and/or triggers that initiate one or more responses to these state changes.

In some embodiments, the environment sensing can include adaptive inclusion of other devices, which are external to the environment, on a selective basis. For example, if a carer brings a medical monitoring device into the environment and then undertakes tests on the monitored person, the data generated may be passed, to the environment monitoring systems. This can result in changes in the configuration of one or more sensors, devices and/or systems involved in monitoring, including the external device, which can result n in changes to one or more patterns being operated by the system in relation to those sensors, devices and/or systems.

In another example a stakeholder may bring a device into the environment, for example a smart phone, and that device may become part of the monitoring arrangement for the duration of its presence in the environment. In some embodiments, the device may be recognized as that belonging to a stakeholder of the person being monitored, for example a friend, care giver and the like, and as such the data collected may be transferred to the system and may not be permanently stored on the device in manner that is accessible other than when that device is in the presence of the person being monitored and/or their environment. For example, the data may be tokenized using cryptographic techniques, such that it can only be read under specific conditions by either the owner of the device, other devices and/or the system.

Figure 8:
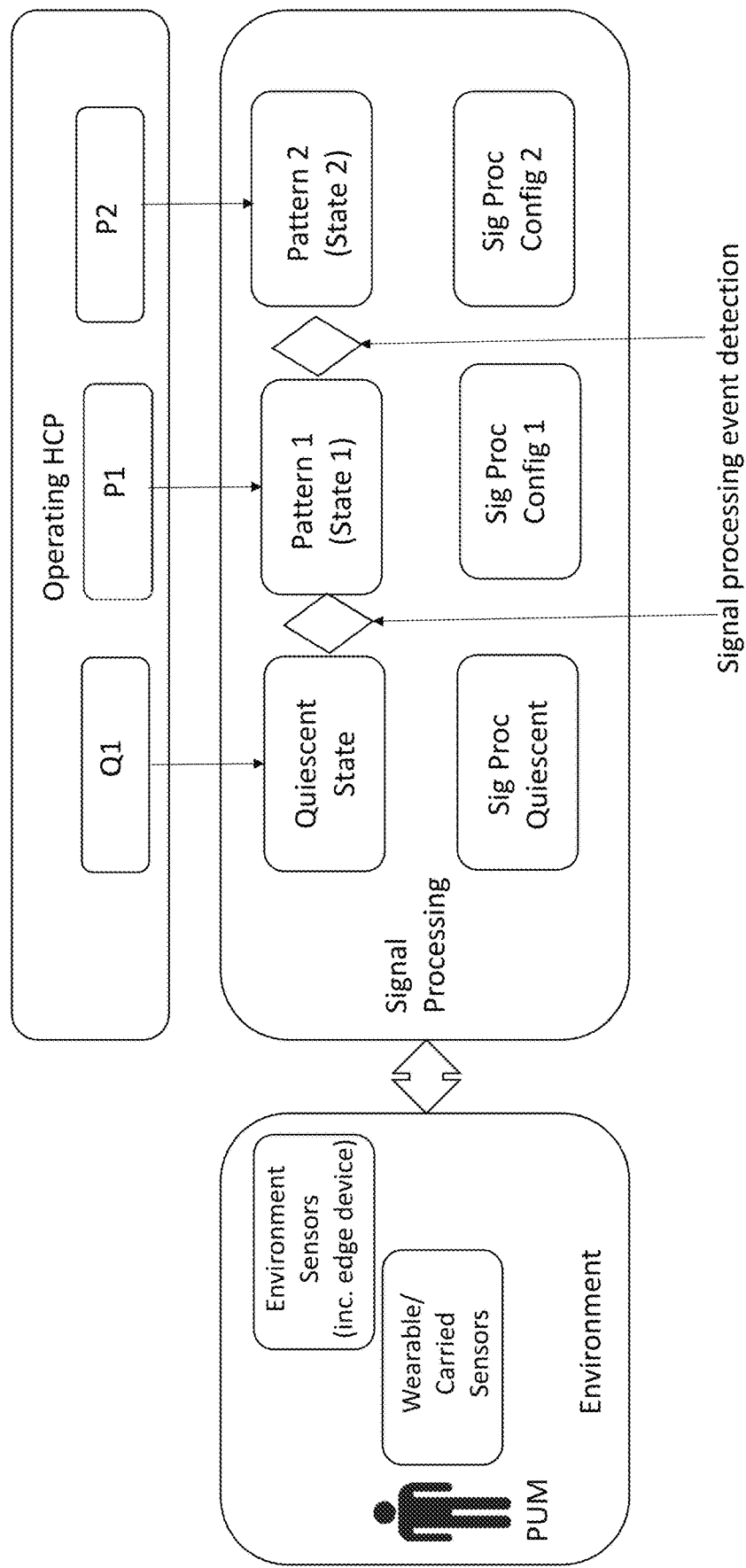
FIG. 8 illustrates an operating HCP (801).

FIG. 8 illustrates an operating HCP 801) comprising a set of states (Q1, P1, P2), including the initial quiescent state (109) for that HCP and/or behavior pattern thereof, which in turn have signal processing configurations (804, 805, 806) pertaining to each of the patterns (802,803) representing those elements of such HCP and/or behavior pattern(s) thereof, such that when signal processing detects an event that represents a change in the state of the environment and/or the PUM, this invokes a change in the pattern that is operating and the signal processing configuration for that pattern.

In some embodiments, an environment can be responsive to the presence or absence of particular stakeholders, for example opening/closing doors/windows, adjusting HVAC and the like.

In some embodiments, a stakeholder who has a profile may visit a PUM, such as when friends and/or family visit a PUM at their domicile or other environment. In this example, their profile can be loaded into sensors, devices and/or systems for the duration of their presence. Depending on the specifications of their profiles and/or those of the PUM, such data can be stored or purged from the sensors, devices and/or systems, for example to protect their and/or the PUM's privacy.

In some embodiments all data storage may be encrypted, using one or more key management systems. This may also be case when data is purged form a system, for example through destruction of the key that encrypts that data and/or through further encryption and key deletion.

Communication Methods.

The communications between sensors, devices and systems includes the sue of standard communications technologies, incusing wireless, wired, near field or other proximity technologies, RF, LASER, visual (including optical), audio and/or any other communications systems with a capability to communicate among and between general and/or specialized devices.

For example, Matter is an industry standard for IoT communications and attempts to integrate multiple communication protocols, such as Wi-Fi, Bluetooth, Zigbee and the like into a common IoT platform. In some embodiments, a sensor, device and/or system may a range of communications methods such as raw data communications, one or more protocols, one or more data compression schema and the like.

In some embodiments, care village systems may deploy a "Care VPN" which is used as a secure communications method between sensors, devices and/or systems that communicate across widely available network infrastructure.

As security of communications in many circumstances is paramount, care village systems may include the use of one or more sets of tokens.

In some embodiments, random sampling of sensors, devices and/or systems data feeds may be used to as a monitoring technique for one or more stakeholder and/or environment, particularly when monitoring a state of quiescence.

In some embodiments there may be a specialist gateway, router, data aggregator, data repository, hub and/or node that supports the monitoring of one or more stakeholders and/or environments. Such device, herein described as a care hub, can provide sensors, devices and/or systems with one or more capabilities, including one or more repository, including an elastic repository capability, processing, communications, management, configuration, aggregation and/or other care village system management capabilities. A care hub can be configured to provide different authorized and/or authenticated sensors, devices, systems and/or stakeholder identities with specific access to one or more data sets. For example, in an emergency situation, medical and/or other emergency response teams may have access to all the data generated by sensors, devices and/or systems involved in monitoring a PUM who is experiencing a medical emergency, including data that is stored in one or more elastic repository which can includes data that is generated by one or more sensor, device and/or system prior to the occurrence of the emergency.

In some embodiments the communications of the care hub for the environment can be configured so as to use differing priorities and communication protocols for differing sensor and/or device arrangements in response to signal processing patterns operating at the time. This can include the use of secured tunnels, TLS and/or VPN's in support of active medical interventions and/or prioritization of a particular sensor output for one or more stakeholders. The care hub may provide stakeholders, sensors, devices and/or systems with one or more tokens that grant access to one or more data sets under one or more governance specifications.

This care hub capability may include the segmentation of multiple sensor data sets, including tokens representing that data to differing stakeholders with differing priorities. For example, a carer may directly receive data in real time and have a channel, including audio, video and/or other sensor data where, for example an operating signal processing pattern and/or a care hub, has configured the sensors and communication systems to provide this information. For example, this may be the case where at least one event has triggered a more highly focused monitoring situation, such as when the person under monitoring has tripped, dropped something or similar. In this example, the carer may be able to have direct communication with the monitored person, and may then decide whether further attention is required and in what timeframe.

In many situations the care system will use standard off the shelf hardware and devices and provide configuration and control software to enable these devices to perform the functionality required. In many cases there are standards for operation of these devices that can be configured for this purpose. A care hub may include API's for both ingestion of data from sensors, devices and/or systems and may provide further API access to other authorized and authenticated entities with which the care hub is in communication.

A key aspect of the care system is the respect for the privacy of the stakeholders therein. This can be of paramount importance for the PUM, where if they feel their "personal space" is being invaded they are less likely to accept the monitoring that can most benefit them as they undergo their journey in an HCP.

The use of tokenization can provide enablement for this privacy protection.

Digital Twins

The system may incorporate digital twins which are representations of environments and the persons therein. These Care Village Digital Twins (CVDT) can initially be created from an environment framework and then populated with data created by one or more sensors in that environment. This is also the case for one or more stakeholders that have relationships with that environment, in that an initial profile is created for them on instantiation as system entities, that is then populated with data sets. This includes the health care profiles (HCP) of those persons, specifically the PUM, and the relevant patterns and pattern frameworks for those persons and their care.

With sufficient information on multiple environments represented as digital twins, quantization and approximation may be used to represent a new environment which is to be monitored. This provides a baseline specification for both the environment and person therein, which can then be refined by the data sets and patterns generated by the sensors operating in that environment.

This supports the use of virtual environments for research, testing, monitoring and sensing improvements and the like. In some embodiments, measuring and the devices for that measuring may be virtualized as part of the digital twin, enabling, for example a health professional and/or other authorized stakeholder to access the data sets generated by such devices. For example, blood pressure, oxygenation, heart response and the like can be monitored by an authorized stakeholder without being present as long as the device is sensing the PUM at the environment.

In some embodiments, an environment framework may be created representing an initial course granularity of the environment and the stakeholders of that environment to be monitored. This may include the location, dimensions, characteristics, facilities, identity, role and other basic data sets for the environment and stakeholders which can include further data sets for the person to be monitored and the stakeholders associated with that person and the monitoring.

As the sensors employed for the monitoring establish the quiescent state for that environment, the environment framework can be populated by data from the sensors, increasing the overall fidelity of the environment framework to a point where the actual situation in the environment can be represented by a CVDT managed and operated by the system.

FIG. 10 illustrates the use of care village digital twins (701) for data ingestion, state management (707), pattern identification (707,708) and determination and/or predictive processing (703), including the sue of ML/A techniques (702).

As the CVDT is populated with both environment and pattern data, the person under monitoring whose care journey unfolds in relation to their HCP. This can be quantized into a set of states, whereby the relative quiescent states that intersperse the patterns are concatenated to provide a series of states over time.

The CVDT may be used in combination with an HCP and one or more pattern for predictive purposes. For example, the CVDT may be configured with additional sensors where a PUM is predicted to be likely to have a care incident, such that the prevention, mitigation and/or detection of that incident is more likely, and as such the environment may be augmented by the configuration of an existing one or more sensor, and/or the addition of further one or more sensors to that environment.

In some embodiments, at least one CVDT can identify and classify synthetic feature sets across one or more sensors, based on data sets provided by signal processing. These synthetic feature sets are sets that are initially represented in at least one CVDT and can then be passed to an arrangement of sensors for monitoring of a PUM and/or the environment. In some embodiments, a synthetic feature set involves features arrangements that each single sensor is not capable of determining, however in concert with an appropriate care analytics management processor a combination of sensors can identify such a synthetic feature set. This extends and expands the operating limitations of the sensor set so as to more accurately determine the behaviors of a PUM in and environment for care monitoring. These synthetic feature sets may then be deployed in operating patterns and/or sensor arrangements In many circumstances the CVDT will be used as part of a predictive analysis based on the behavior patterns detected, for a PUM in an HCP. In this example, the CVDT provides a representation of the environment that is sufficiently detailed to enable the system to evaluate the behavioral characteristics being exhibited by a PUM, so as to ascertain the appropriate one or more patterns to be deployed. This can involve multiple CVDT of a single environment being evaluated simultaneously with differing patterns to ascertain the best match to the behaviors being monitored.

The use of CVDTs as a method for representation of the environment, PUM and patterns over a period of time can provide a visualization and representation of the care journey for the PUM. This can be used for research, analysis and/or discovery of behaviors, patterns or other information sets pertaining to the specific PUM and/or environment and/or an aggregation of similar PUM and/or environments to discover further patterns, care issues and the like.

The same mechanism can be used to forecast the care journey of a PUM to establish the likely needs and requirements of the PUM as they traverse their current HCP patterns and move to a further pattern and/or HCP. This capability supports the creation of care regimes, financial planning and eventually hospice or other palliative care planning. The information generated through such CVDT analytics may be used to inform medical practitioners supporting the PUM of specific forthcoming care incidents, medication requirements, physical and mental limitations and the like.

This capability can be used for resource planning, risk management, fraud detection, financial management and implications, automatic and/or other provisioning, product and/or service promotion and provisioning and the like.

CVDT can always be operating to provide constant representations of the monitoring and using ML/AI techniques, and can instantiate multiple threaded possible behaviors, patterns and/or other situation matching.

Such an approach allows for one or monitoring system to step back and forward in the timeline, which in turn can support stakeholders, including the PUM, having the presentation and visualization of this data so as enable evaluation and understanding of the relative position of a person in their HCP journey In some embodiments, there may be multiple PUM, all in differing, though is some examples, such as a care facility, similar environments. Each of these unique PUM may have HCP operating that are the same or have a number of similar attributes, characteristics and/or features. Each of these may then have a CVDT and the data sets from the PUM and their environments may undergo one or more evaluations employing one or more machine learning techniques. This can result in the identification of patterns that are applicable, at least in part, to all of the PUM being monitored. In this way new patterns may be determined and identified, including those that could not have been so identified by data from a single PUM in a single environment.

Figure 9:
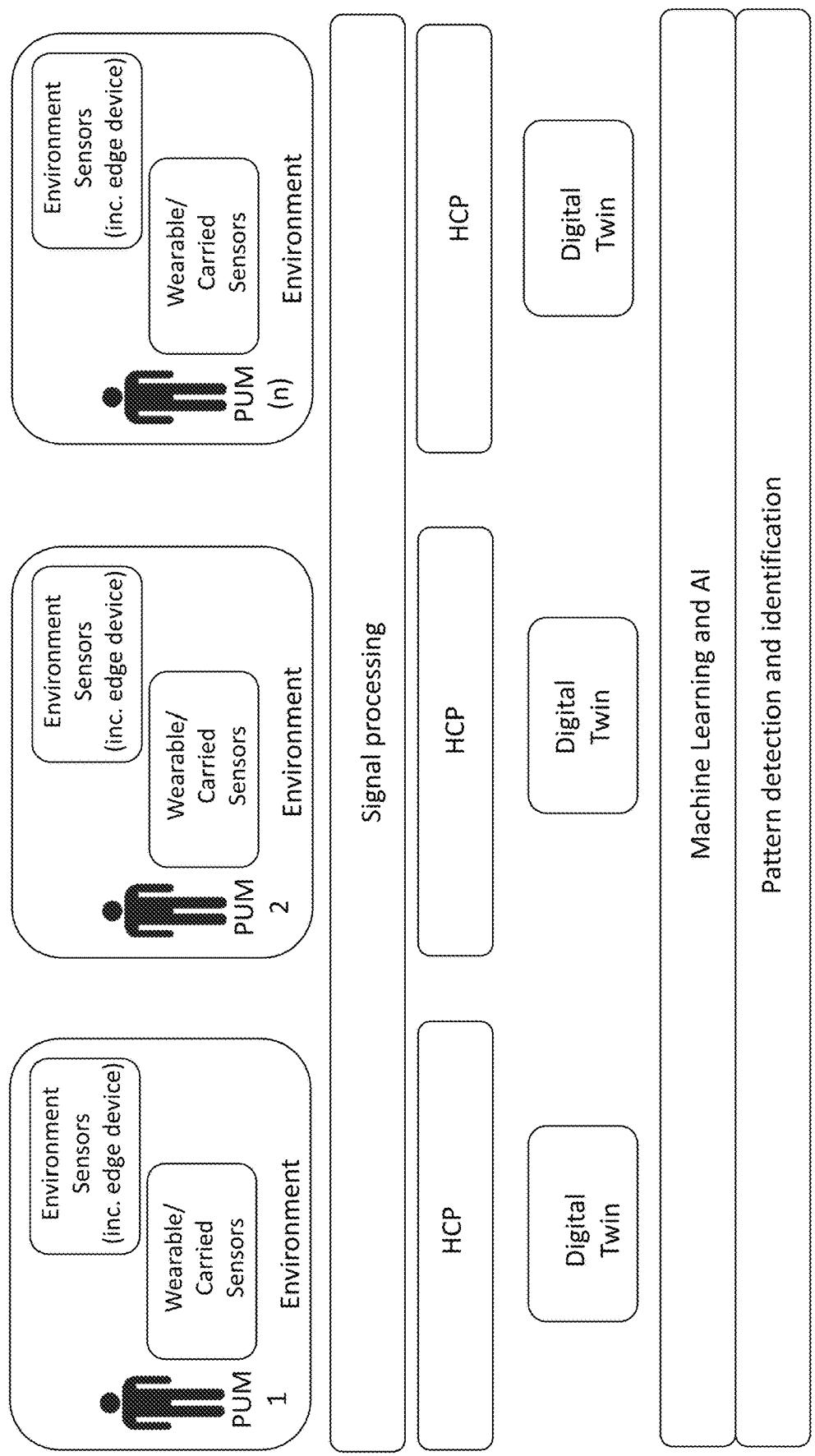
FIG. 9 illustrates a number of PUM (901, 911, 921), each domiciled in a differing environment (902, 912, 922).

FIG. 9 illustrates a number of PUM (901, 911, 921), each domiciled in a differing environment (902, 912, 922), each of which HCP (906, 916, 926) are common and/or have sufficient common attributes, each of which has a care village digital twin (907, 917, 927) representing that PUM, their HCP, current operating pattern and signal processing (905) configuration and/or state, such that one or more machine learning module (908) may evaluate such representations to identify, determine and classify patterns (909) that are common to all PUM being evaluated.

What is claimed is:

1. A system to monitor a person under care by at least one carer, comprising:
    a care analytics management processor;
    a plurality of micro-electromechanical systems (MEMS) microphones and haptic sensors, each of the MEMS microphones and haptic sensors including at least one repository configured to store a dynamically configured predetermined amount of sensed data from an environment of the person under care, connected to a non-transitory computer readable storage medium for storage of data generated by the MEMS microphones or the haptic sensors, the MEMS microphones and the haptic sensors each configured to:
    sense the environment of the person under care,
    determine a quiescent state of the environment of the person under care,
    detect an edge condition deviating from the quiescent state resulting in edge condition data,
    upon detection of the edge condition, the MEMS microphone or the haptic sensor is configured to evaluate the data held in the at least one elastic repository and the edge condition to determine whether the MEMS microphone or the haptic sensor changes to an active state,
    upon changing to an active state, the MEMS microphone or the haptic sensor transmits a configuration specification to at least one other sensor in the plurality of MEMS microphones and haptic sensors in proximity to the MEMS microphone or haptic sensor, and
    wherein the MEMS microphone or the haptic sensor in the active state transmits the sensed data and the edge condition data to the care analytics management processor;
    the care analytics management processor, further comprising:
    a transceiver configured to receive the sensed data and the edge condition data, and
    at least one microprocessor to determine whether a false positive situation has occurred, and
    when the false positive situation has occurred, the transceiver is configured to transmit the configuration specification to reset the plurality of MEMS microphones and the haptic sensors into the quiescent state, or
    when a positive situation has occurred, the care analytics management processor is configured to transmit an alert to the at least one stakeholder.

2. The system of claim 1, wherein at least one of plurality of MEMS microphones is attached to a hard surface.

3. The system of claim 2, wherein the hard surface is a window.

4. The system of claim 2, wherein the hard surface is a floor.

5. The system of claim 2, wherein the hard surface is a kitchen appliance door.

6. The system of claim 2, wherein the hard surface is a ceiling.

7. The system of claim 2, wherein the hard surface is a wall.

8. The system of claim 2, wherein the at least one of plurality of MEMS microphones is used to track acoustic events.

9. The system of claim 8, wherein at least one microprocessor used the acoustic events to acoustic fingerprint the environment of the person under care.

10. The system of claim 2, wherein the at least one of plurality of MEMS microphones is configured to monitor a footfall of the person under care.

11. The system of claim 10, wherein the at least one of plurality of MEMS microphones is configured to monitor a fall of the person under care.

12. The system of claim 2, wherein at least one of the haptic sensors acts as a strain gauge.

13. The system of claim 12, wherein the strain gauge is configured to detect pressure on a hard surface.

14. The system of claim 2, wherein the at least one of plurality of MEMS microphones is configured using a voice recognition technique.

15. The system of claim 1, wherein the care analytics management processor determines that a false negative has occurred by analyzing the sensed data and the edge condition data from more than one of the MEMS microphones.

16. The system of claim 1, wherein at least one of the plurality of MEMS microphones configures at least one active emission sensor device configured to create a map of the environment.

17. The system of claim 16, wherein the map of the environment is a 3-dimensional model.

18. The system of claim 17, wherein the 3-dimensional model is transformed into a digital twin of the environment.

19. The system of claim 1, further comprising:
a plurality of cameras, each of the plurality of cameras configured to:
sense the environment of the person under care,
determine the quiescent state of the environment of the person under care,
detect the edge condition deviating from the quiescent state resulting in edge condition data,
upon detection of the edge condition, the camera is configured to evaluate the data held in the at least one elastic repository and the edge condition to determine whether the camera changes to an active state,
upon changing to an active state, the camera transmits a configuration specification to at least one other sensor in the plurality of MEMS microphones, haptic sensors or cameras in proximity to the camera, and
wherein the camera in the active state transmits the sensed data and the edge condition data to the care analytics management processor.

20. The system of claim 19, wherein the transceiver is further configured to transmit the configuration specification to reset the plurality of cameras into the quiescent state when the false positive situation has occurred.

21. A method, comprising:
storing, in an elastic repository, a dynamically configured predetermined amount of sensed data from an environment of a person under care, sensed via a plurality of micro-electromechanical systems (MEMS) microphones and haptic sensors;
determining a quiescent state of the environment of the person under care;
in response to detecting an edge condition deviating from the quiescent state resulting in edge condition data, evaluating the sensed data held in the elastic repository and the edge condition to determine whether to change at least one of the MEMS microphones or haptic sensors from a quiescent state to an active state;
in response to changing the at least one of the MEMS microphones or haptic sensors to the active state, transmitting a configuration specification to at least one other MEMS microphone or haptic sensor in the plurality of MEMS microphones and haptic sensors in proximity to the at least one of the MEMS microphones or haptic sensors;
determining whether a false positive situation has occurred, based on the sensed data and the edge condition data;
in response to determining that the false positive situation has occurred, resetting the plurality of MEMS microphones and haptic sensors to the quiescent state; and
in response to determining that a positive situation has occurred, transmitting an alert to a stakeholder of the person under care.

* * * * *